(12) United States Patent
Kumata

(10) Patent No.: US 11,793,489 B2
(45) Date of Patent: Oct. 24, 2023

(54) ULTRASOUND ENDOSCOPE WITH FLEXURE RELAY SUBSTRATE

(71) Applicant: Olympus Corporation, Tokyo (JP)

(72) Inventor: Yuya Kumata, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 151 days.

(21) Appl. No.: 16/817,706

(22) Filed: Mar. 13, 2020

(65) Prior Publication Data

US 2020/0205777 A1  Jul. 2, 2020

Related U.S. Application Data

(63) Continuation of application No. PCT/JP2018/034523, filed on Sep. 18, 2018.

(30) Foreign Application Priority Data

Sep. 20, 2017 (JP) ................. 2017-180380

(51) Int. Cl.
*A61B 8/00* (2006.01)
*A61B 8/12* (2006.01)
*A61B 1/04* (2006.01)

(52) U.S. Cl.
CPC .............. *A61B 8/4494* (2013.01); *A61B 8/12* (2013.01); *A61B 1/04* (2013.01)

(58) Field of Classification Search
CPC ..... A61B 8/12; A61B 8/4494; A61B 17/2202; A61B 2017/22021; A61B 8/4444–4483
See application file for complete search history.

(56) References Cited

U.S. PATENT DOCUMENTS

2009/0093725 A1  4/2009  Sato et al.
2017/0143298 A1*  5/2017  Kitahara ................ A61B 8/445
(Continued)

FOREIGN PATENT DOCUMENTS

JP  2517331 B2  7/1996
JP  2555376 B2 * 11/1996
(Continued)

OTHER PUBLICATIONS

International Search Report dated Nov. 20, 2018 issued in International Application No. PCT/JP2018/034523.

*Primary Examiner* — Yi-Shan Yang
*Assistant Examiner* — Neshat Baset
(74) *Attorney, Agent, or Firm* — Scully, Scott, Murphy & Presser, P.C.

(57) ABSTRACT

An ultrasound endoscope includes: a distal end portion that is provided on a distal end of an insertion portion; a curvature portion that is connected to a proximal end side of the distal end portion in the insertion portion; a plurality of coaxial wires that are inserted into the curvature portion; a convex ultrasound transducer provided in the distal end portion; and a relay substrate that is disposed in the distal end portion, is connected to the ultrasound transducer, and is connected to the coaxial wires. The relay substrate includes a first surface that is connected to the ultrasound transducer, a second surface that is connected to the coaxial wires, and a third surface that is continuous to the first surface through a first flexure portion and is continuous to the second surface through a second flexure portion.

6 Claims, 17 Drawing Sheets

(56) References Cited

U.S. PATENT DOCUMENTS

| | | | |
|---|---|---|---|
| 2018/0132820 A1* | 5/2018 | Irie | A61B 8/4483 |
| 2018/0153508 A1* | 6/2018 | Kandori | B06B 1/0292 |
| 2018/0168541 A1* | 6/2018 | Kitahara | A61B 8/12 |

FOREIGN PATENT DOCUMENTS

| | | | | |
|---|---|---|---|---|
| JP | 2007-330351 A | | 12/2007 | |
| JP | 5491717 B2 | * | 5/2014 | |
| JP | 2015-208378 A | | 11/2015 | |
| JP | 2015208378 A | * | 11/2015 | |
| JP | 2016-002200 A | | 1/2016 | |
| WO | WO-2016130713 A1 | * | 8/2016 | A61B 5/6852 |

* cited by examiner

ULTRASOUND ENDOSCOPE WITH FLEXURE RELAY SUBSTRATE

CROSS-REFERENCE TO RELATED APPLICATION

This application is a continuation of PCI International Application No. PCT/JP2018/034523 filed on Sep. 18, 2018, which designates the United States, incorporated herein by reference, and which claims the benefit of priority from Japanese Patent Application No. 2017-180380, filed on Sep. 20, 2017, incorporated herein by reference.

BACKGROUND

1. Technical Field

The present disclosure relates to an ultrasound endoscope provided with an insertion portion to be inserted into a subject.

2. Related Art

In the related art, in a medical field, an endoscope system is used at the time of observing the internal organ of a subject such as a patient. The endoscope system, for example, includes an endoscope provided with an image sensor that is provided on a distal end, and an insertion portion that is inserted into the subject, and a processing device that is connected to a proximal end side of the insertion portion through a cable, performs image processing with respect to an in-vivo image according to an imaging signal generated by the image sensor, and displays the in-vivo image on a display unit or the like. The insertion portion includes a curvature portion that is provided on a proximal end side of the distal end portion in which the image sensor is provided, and can be curved.

In the endoscope, the image sensor and a signal cable are connected to each other through a flexible substrate that can be bent (for example, refer to JP 2016-2200 A). According to JP 2016-2200 A, the flexible substrate is bent with respect to a load applied from the outside, and thus, a stress applied to a connection portion between the image sensor and the flexible substrate due to the load can be relaxed. When the curvature portion is curved along a direction in which the flexible substrate is bent, the endoscope disclosed in JP 2016-2200 A is capable of relaxing a stress due to the curvature.

SUMMARY

In some embodiments, an ultrasound endoscope includes: a distal end portion that is provided on a distal end of an insertion portion to be inserted into a subject; a curvature portion that is connected to a proximal end side of the distal end portion in the insertion portion, and is capable of being curved in two directions orthogonal to each other; a plurality of coaxial wires that are inserted into the curvature portion in a longitudinal axis direction of the insertion portion; a convex ultrasound transducer including two surfaces where one surface is configured to transmit and receive an ultrasound and another surface is an opposite surface that is on a side opposite to the one surface, the convex ultrasound transducer being provided in the distal end portion so as to incline the opposite surface with respect to the longitudinal axis; and a relay substrate that is disposed in the distal end portion, is connected to the ultrasound transducer, and is connected to the coaxial wires, the relay substrate being configured to relay transmission of an electric signal to each of the coaxial wires from the ultrasound transducer. The relay substrate includes a first surface that as connected to the ultrasound transducer, and extends from the opposite surface of the ultrasound transducer, a second surface that is connected to the coaxial wires, and a third surface that is disposed to face the opposite surface of the ultrasound transducer, is continuous to the first surface through a first flexure portion, and is continuous to the second surface through a second flexure portion that is bent in a direction orthogonal to the first flexure portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
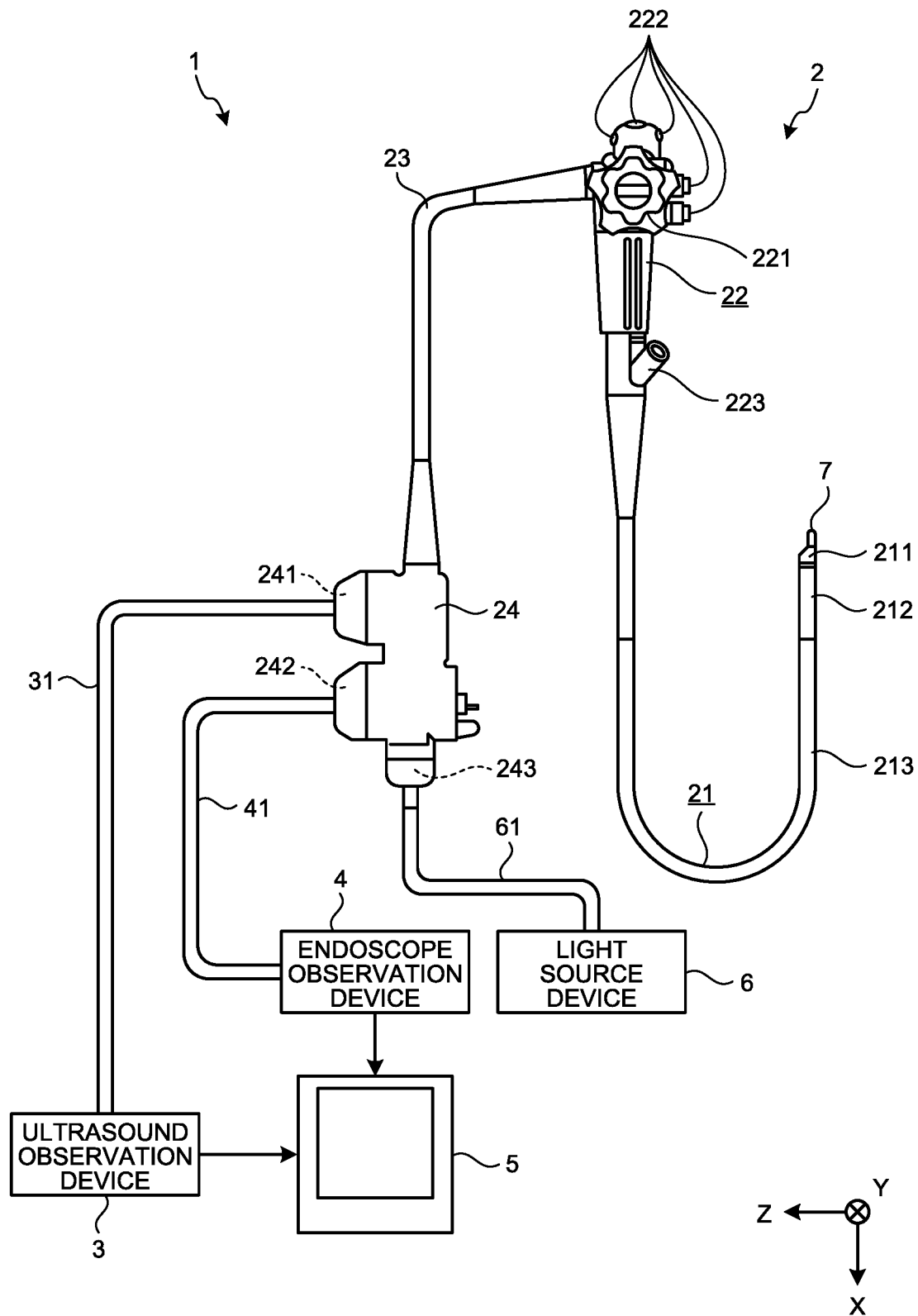
FIG. 1 is a diagram schematically illustrating an endoscope system according to a first embodiment of the disclosure.

Hereinafter, modes for carrying out the disclosure (hereinafter, embodiments) will be described with reference to the drawings. Note that, the disclosure is not limited to the embodiments described below. Further, in the description of the drawings, the same reference numerals are applied to the same portions.

First Embodiment

FIG. 1 is a diagram schematically illustrating an endoscope system according to a first embodiment of the disclosure. An endoscope system 1 is a system that performs ultrasound diagnosis with respect to the inside of a subject such as a person by using an ultrasound endoscope. As illustrated in FIG. 1, the endoscope system 1 includes an ultrasound endoscope 2, an ultrasound observation device 3, an endoscope observation device 4, a display device 5, and a light source device 6.

The ultrasound endoscope 2 converts an electric pulse signal that is received from the ultrasound observation device 3 into an ultrasound pulse (an acoustic pulse) by an ultrasound transducer that is provided on a distal end portion and irradiates the subject with the pulse, and converts an ultrasound echo that is reflected on the subject into an electric echo signal that is represented by a voltage change and outputs the signal.

The ultrasound endoscope 2 includes an imaging optical system and an image sensor, is inserted into the digestive canal (the esophagus, the stomach, the duodenum, and the large intestine) or the apparatus respiratorius (the trachea and the bronchial tube) of the subject, and is capable of capturing any of the digestive canal and the apparatus respiratorius. The ultrasound endoscope 2 includes a light guide that guides illumination light emitted to the subject at the time of capturing. In the light guide, a distal end portion reaches a distal end of an insertion portion of the ultrasound endoscope 2 with respect to the subject, and a proximal end portion is connected to the light source device 6 that emits the illumination light. In addition, the ultrasound endoscope 2 transmits an ultrasound to the surrounding internal organ of the digestive canal or the apparatus respiratorius (the pancreas, the bladder, the bile duct, the bile passage, the lymphaden, the mediastinum internal organ, the blood vessel, and the like), and receives the ultrasound that reflected on the surrounding internal organ.

As illustrated in FIG. 1, the ultrasound endoscope 2 includes an insertion portion 21, an operating unit 22, a universal code 23, and a connector 24. The insertion portion 21 is a portion that is inserted into the subject. As illustrated in FIG. 1, the insertion portion 21 includes a rigid distal end portion 211 that is provided on the distal end side and includes an ultrasound transducer 7, a curvature portion 212 that is linked to a proximal end side of the distal end portion 211 and can be curved, and a flexible tube portion 213 that is linked to a proximal end side of the curvature portion 212 and has flexibility. Here, although it is not specifically illustrated, a plurality of signal lines that include the light guide transmitting the illumination light supplied from the light source device 6 and a signal line described below (a coaxial wire 81) and transmit various signals are routed, and an insertion passage for a treatment tool for inserting a treatment tool, and the like are formed, in the insertion portion 21. The curvature portion 212 is capable of curving a longitudinal axis of the distal end portion 211 in two directions different from each other. The curvature portion 212, for example, is capable of changing the direction of the distal end portion 211 by being curved on an XY plane illustrated in FIG. 1, and is capable of changing the direction of the distal end portion 211 by being curved on an XZ plane orthogonal to the XY plane.

The ultrasound transducer 7 is a convex ultrasound transducer in which a plurality of piezoelectric elements are provided into the shape of an array, and the piezoelectric elements involved in transmission and reception are electronically switched or transmission and reception of each of the piezoelectric elements are delayed, and thus, electronic scanning is performed. The configuration of the ultrasound transducer 7 will be described below.

Figure 2:
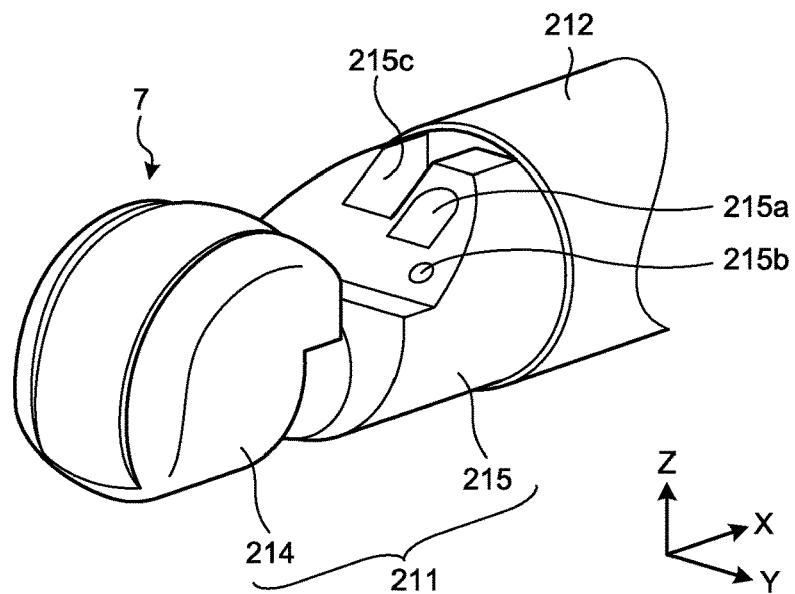
FIG. 2 is a perspective view schematically illustrating a distal end configuration of an insertion portion of an ultrasound endoscope according to the first embodiment of the disclosure.

FIG. 2 is a perspective view schematically illustrating the distal end configuration of the insertion portion of the ultrasound endoscope according to the first embodiment. As illustrated in FIG. 2, the distal end portion 211 includes an ultrasound transducer module 214 that retains the ultrasound transducer 7, an endoscope module 215 including an objective lens 215a that forms a part of the imaging optical system and takes light from the outside, an image sensor, and an illumination lens 15b that condenses the illumination light and allows the light to exit to the outside. In the endoscope module 215, a treatment tool protrusion port 215c that is communicated with the insertion passage for a treatment tool formed in the insertion portion 21, and allows the treatment tool to protrude from the distal end of the insertion portion 21 is formed. In the insertion passage for a treatment tool, the vicinity of the end portion continuous to the treatment tool protrusion port 215c is inclined with respect to the longitudinal axis of the insertion portion 21, and the treatment tool protrudes in a direction inclined with respect to the longitudinal axis, from the treatment tool protrusion port 215c. Here, the longitudinal axis is an axis along a longitudinal direction of the insertion portion 21. In the curvature portion 212 or the flexible tube portion 213, an axis direction is changed in accordance with each position, but in the rigid distal end portion 211, the longitudinal axis is an axis that forms a constant straight line.

Returning to FIG. 1, the operating unit 22 is a unit that is linked to the proximal end side of the insertion portion 21, and receives various operations from a user such as a medical doctor. As illustrated in FIG. 1, the operating unit 22 includes a curvature knob 221 for performing a curvature operation with respect to the curvature portion 212, and a plurality of operation members 222 for performing various operations. In addition, in the operating unit 22, a treatment tool insertion port 223 for inserting the treatment tool into the insertion passage for a treatment tool that is communicated with the insertion passage for a treatment tool is formed.

The universal code 23 is a cable extending from the operating unit 22 in which a plurality of signal cables for transmitting various signals, an optical fiber for transmitting the illumination light supplied from the light source device 6, and the like are disposed.

The connector 24 is provided on a distal end of the universal code 23. Then, the connector 24 includes a first connector portion to a third connector portion 241 to 243 to which an ultrasound cable 31, a video cable 41, and an optical fiber cable 61 are respectively connected.

The ultrasound observation device 3 is electrically connected to the ultrasound endoscope 2 through the ultrasound cable 31 (FIG. 1), outputs a pulse signal to the ultrasound endoscope 2 through the ultrasound cable 31, and inputs an echo signal from the ultrasound endoscope 2. Then, the ultrasound observation device 3 performs predetermined processing with respect to the echo signal, and generates ultrasound image data.

The endoscope observation device 4 is electrically connected to the ultrasound endoscope 2 through the video cable 41 (refer to FIG. 1), and inputs an image signal from the ultrasound endoscope 2 through the video cable 41. Then, the endoscope observation device 4 performs predetermined processing with respect to the image signal, and generates endoscope image data.

The display device 5 is configured by using a liquid crystal or organic electro luminescence (EL), a projector, a cathode ray tube (CRT), and the like, and displays an ultrasound image that is generated by the ultrasound observation device 3, an endoscope image that is generated by the endoscope observation device 4, or the like.

The light source device 6 is connected to the ultrasound endoscope 2 through the optical fiber cable 61 (refer to FIG. 1), and supplies the illumination light that illuminates the inside of the subject to the ultrasound endoscope 2 through the optical fiber cable 61.

Figure 3:
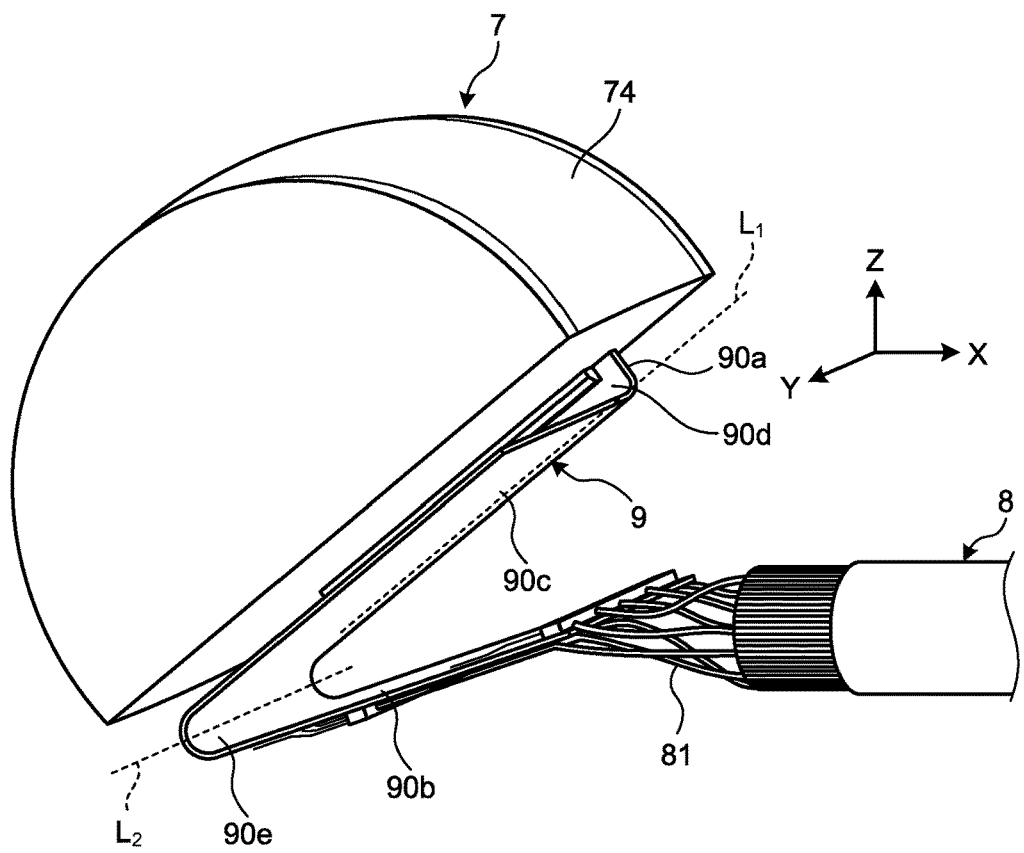
FIG. 3 is a perspective view schematically illustrating an internal configuration of a distal end portion in the ultrasound endoscope according to the first embodiment of the disclosure.
Figure 4:
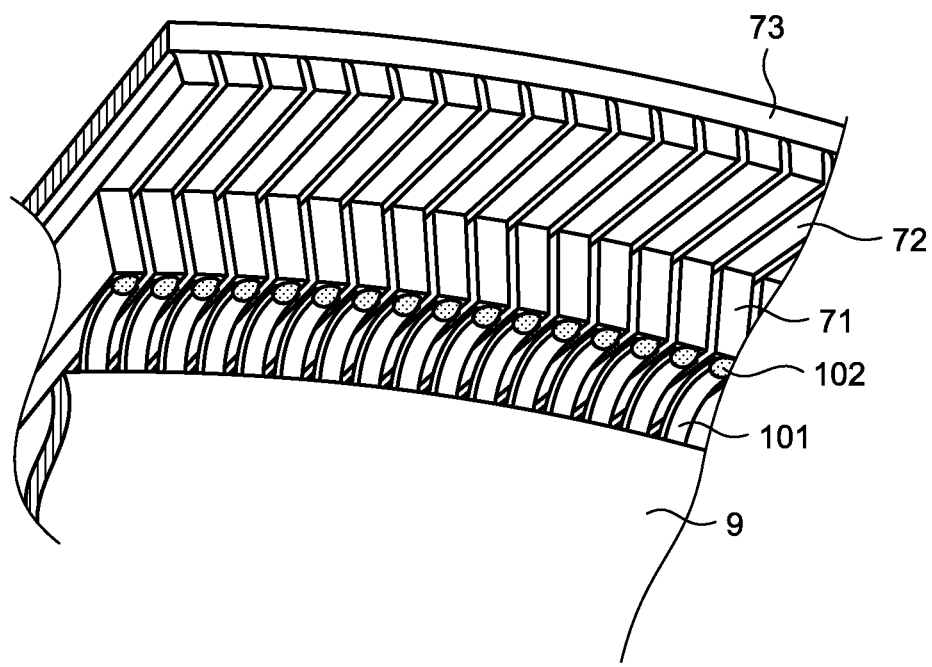
FIG. 4 is a view describing a configuration of an ultrasound transducer illustrated in FIG. 3.

Subsequently, the configuration of the ultrasound transducer 7 provided on the distal end of the insertion portion 21 will be described with reference to FIGS. 3 and 4. FIG. 3 is a perspective view schematically illustrating an internal configuration of the distal end portion 211 in the ultrasound endoscope according to the first embodiment. FIG. 4 is a view describing the configuration of the ultrasound transducer 7 illustrated in FIG. 3. In the first embodiment, it is described that the ultrasound transducer 7 is the convex ultrasound transducer illustrated in FIG. 2, and is a one-dimensional array (a 1D array) in which a plurality of piezoelectric elements 71 are arranged in line. In other words, in the ultrasound transducer 7 according to the first embodiment, the plurality of piezoelectric elements 71 are arranged by being curved along an outer surface that forms a curved surface of the ultrasound transducer 7, include the longitudinal axis, and transmit and receive an ultrasound on a surface parallel to the longitudinal axis (for example, the XZ plane).

The ultrasound transducer 7 includes the plurality of piezoelectric elements 71 that are in the shape of a prism and are aligned in the longitudinal direction, a first acoustic matching layer 72 that is provided on the outer surface side of the ultrasound transducer 7 with respect to the piezoelectric element 71, a second acoustic matching layer 73 that is provided on the first acoustic matching layer 72 on a side opposite to a side in contact with the piezoelectric element 71, and an acoustic lens 74 that is provided on the second acoustic matching layer 73 on a side opposite to a side in contact with the first acoustic matching layer 72 (refer to FIG. 3). A backing material (not illustrated) is provided on the piezoelectric element 71 on a side opposite to a side in contact with the first acoustic matching layer 72. The backing material attenuates an unnecessary ultrasound vibration that is generated by the operation of the piezoelectric element 71. The backing material is formed by using a material having a large attenuation rate, for example, an epoxy resin in which fillers such as alumina or zirconia are dispersed, or rubber in which the fillers described above are dispersed.

In FIG. 4, the piezoelectric element 71 converts an electric pulse signal into an acoustic pulse and irradiates the subject with the pulse, and converts an ultrasound echo reflected on the subject into an electric echo signal that is represented by a voltage change and outputs the signal. The piezoelectric element 71 is connected to an ultrasound cable 8 that is electrically connected to the ultrasound cable 31 (refer to FIG. 3). The ultrasound cable 8 includes a plurality of coaxial wires 81. Each of the coaxial wires 81 is electrically connected to the corresponding piezoelectric element 71 through a relay substrate 9 described below. Note that, in FIG. 3, a configuration that is simplified in order for the description is illustrated, but the actual coaxial wire is provided in accordance with the number of piezoelectric elements 71.

The first acoustic matching layer 72 and the second acoustic matching layer 73 match acoustic impedance of the piezoelectric element 71 with acoustic impedance of an observation target such that a sound (an ultrasound) is efficiently transmitted between the piezoelectric element 71 and the observation target. The first acoustic matching layer 72 and the second acoustic matching layer 73 are formed of materials different from each other. Note that, in the first embodiment, it is described that there are two acoustic matching layers (the first acoustic matching layer 72 and the second acoustic matching layer 73), but there may be only one layer or may be three or more layers, in accordance with the properties of the piezoelectric element 71 and the observation target.

The acoustic lens 74 covers an outer surface of the first acoustic matching layer 72 and the second acoustic matching layer 73. The acoustic lens 74 forms the outer surface of the ultrasound transducer 7. The acoustic lens 74 is formed by using silicone, polymethyl pentene, an epoxy resin, polyether imide, and the like, includes one surface that is formed into a convex or concave shape and has a function of narrowing down an ultrasound, and allows an ultrasound that passes through the second acoustic matching layer 73 to exit to the outside or takes an ultrasound echo from the outside. The acoustic lens 74 can be arbitrarily provided, and the acoustic lens 74 may not be provided.

The piezoelectric element 71 is vibrated by the input of a pulse signal, and thus, the ultrasound transducer 7 having the configuration described above irradiates the observation target with an ultrasound through the first acoustic matching layer 72, the second acoustic matching layer 73, and the acoustic lens 74. At this time, in the piezoelectric element 71, an unnecessary ultrasound vibration from the piezoelectric element 71 is attenuated by the backing material, on a side opposite to a side where the first acoustic matching layer 72, the second acoustic matching layer 73, and the acoustic lens 74 are disposed. In addition, an ultrasound reflected from the observation target is transmitted to the piezoelectric element 71 through the acoustic lens 74, the second acoustic matching layer 73, and the first acoustic matching layer 72. The piezoelectric element 71 is vibrated by the transmitted ultrasound, and the piezoelectric element 71 converts the vibration into an electric echo signal and outputs the signal to the ultrasound observation device 3.

The ultrasound transducer module 214 includes the relay substrate 9 that relays electric connection between the ultrasound transducer 7 and the plurality of coaxial wires 81 forming a part of a path electrically connecting the ultrasound transducer 7 (the ultrasound transducer module 214) and the ultrasound observation device 3 (refer to FIG. 3). As illustrated in FIG. 4, in the relay substrate 9, a lead 101 is electrically connected to a connection portion of the piezoelectric element 71 by a solder 102, on one end side of the piezoelectric element 71 that is a side opposite to a surface transmitting and receiving an ultrasound. The relay substrate 9 is configured by using a flexible substrate (flexible printed circuits: FPC), and can be modified in accordance with a load from the outside. The relay substrate 9 is electrically connected to the plurality of coaxial wires 81 that are inserted into the ultrasound cable 8. The relay substrate 9 is formed by providing a wiring pattern in a strip-like base material that is formed by using polyimide. Hereinafter, a surface of the relay substrate 9 having the widest area is referred to as a "main surface".

The relay substrate 9 includes a first portion 90a extending from the ultrasound transducer 7, a second portion 90b connected to the ultrasound cable 8, and a third portion 90c forming a transmission path of an electric signal between the first portion 90a and the second portion 90b. The relay substrate 9 is formed by using one substrate.

The third portion 90c includes a flexure portion 90d (a first flexure portion) that is continuous to the first portion 90a, and a flexure portion 90e (a second flexure portion) that is bent in a direction different from that of the flexure portion 90d and is continuous to the second portion 90b.

Figure 5:
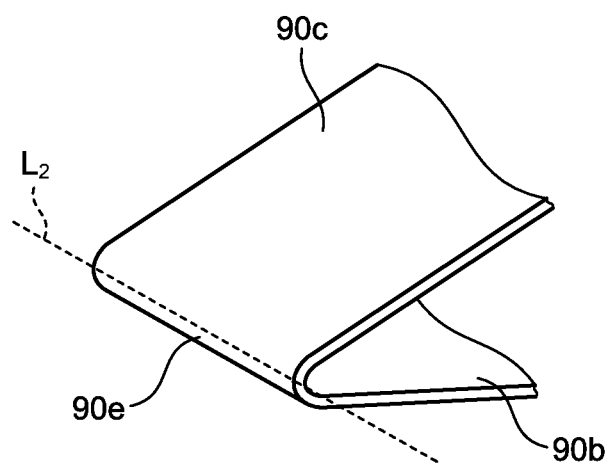
FIG. 5 is a view describing a flexure mode of a relay substrate illustrated in FIG. 3.
Figure 6:
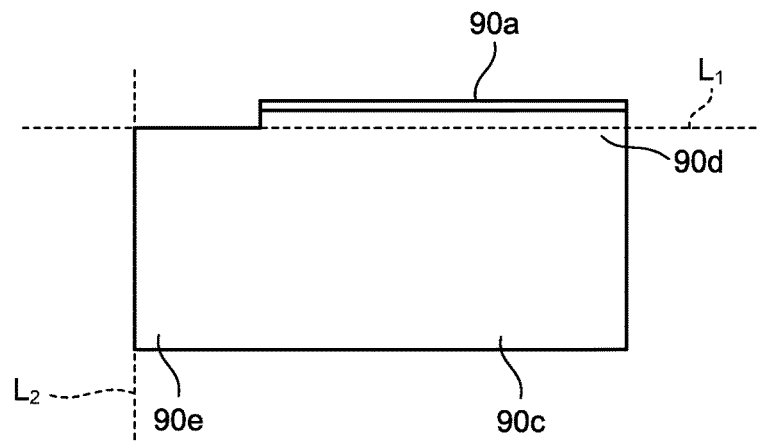
FIG. 6 is a view describing the flexure mode of the relay substrate illustrated in FIG. 3.

FIG. 5 is a view describing a flexure mode of the relay substrate illustrated in FIG. 3, and is an enlarged view of the flexure portion 90e. FIG. 6 is a view describing the flexure mode of the relay substrate illustrated in FIG. 3, and is a plan view when the relay substrate 9 is seen from a direction orthogonal to a main surface of the third portion 90c that is positioned between the flexure portions 90d and 90e.

The flexure portions 90d and 90e are bent is directions orthogonal to each other. Specifically, a straight line $L_1$ extending along a ridge line of a flexure end portion of the flexure portion 90d (a first straight line) and a straight line $L_2$ extending along a ridge line of a flexure end portion of the flexure portion 90e (a second straight line) are orthogonal to each other, in the plan view seen from a direction orthogonal to a main surface extending between the flexure portions 90d and 90e. In the first embodiment, the main surface extending between the flexure portions 90d and 90e is a main surface of the third portion 90c. As illustrated in FIGS. 5 and 6, the straight line $L_2$ extends along the ridge line of the flexure end portion of the flexure portion 90e. Here, the flexure end portion is an end portion of a portion that protrudes due to flexure. The ridge line is a line extending in a width direction of the relay substrate 9, along the protrude end portion. Herein, the width direction is a direction extending along a main surface of the relay substrate, and is a direction orthogonal to the longitudinal direction (a transverse direction). Note that, similarly, the straight line $L_1$ extends along the ridge line of the flexure end portion of the flexure portion 90d.

In such flexure portions 90d and 90e, a vector in the same direction as that or a stress vector or a stress that is generated by the curvature of the curvature portion 212 is represented by a normal vector of a tangent plane that is tangent to the flexure portion 90d (a first tangent plane), and a normal vector of a tangent plane that is tangent to the flexure portion 90e (a second tangent plane), as components. That is, in the stress that is generated by the curvature of the curvature portion 212, the flexure portion 90d is curved by a stress perpendicular to the tangent plane that is tangent to the flexure portion 90d (the first tangent plane), and the flexure portion 90e is curved by a stress perpendicular to the tangent plane that is tangent to the flexure portion 90e (the second tangent plane), and thus, a stress on the relay substrate 9 is reduced.

As described above, the relay substrate 9 according to the first embodiment is bent in each of two different directions by the flexure portion 90d and the flexure portion 90e. According to the first embodiment, even in a case where the curvature portion 212 is curved on the XY plane or is curved on the XZ plane at the time of being curved, two flexure portions of which the flexure directions are different from each other (the flexure portions 90d and 90e) are bent in accordance with the curvature, and thus, it is possible to relax the stress that is generated by the curvature. As described above, in the first embodiment, even in a case where the curvature portion that can be curved in two directions is curved in any direction, it is possible to relax a stress on the connection portion of the flexible substrate. By relaxing the stress that is generated by the curvature, it is possible to suppress disconnection or the like of the coaxial wire, and to improve the reliability of the ultrasound endoscope.

Second Embodiment

Figure 7:
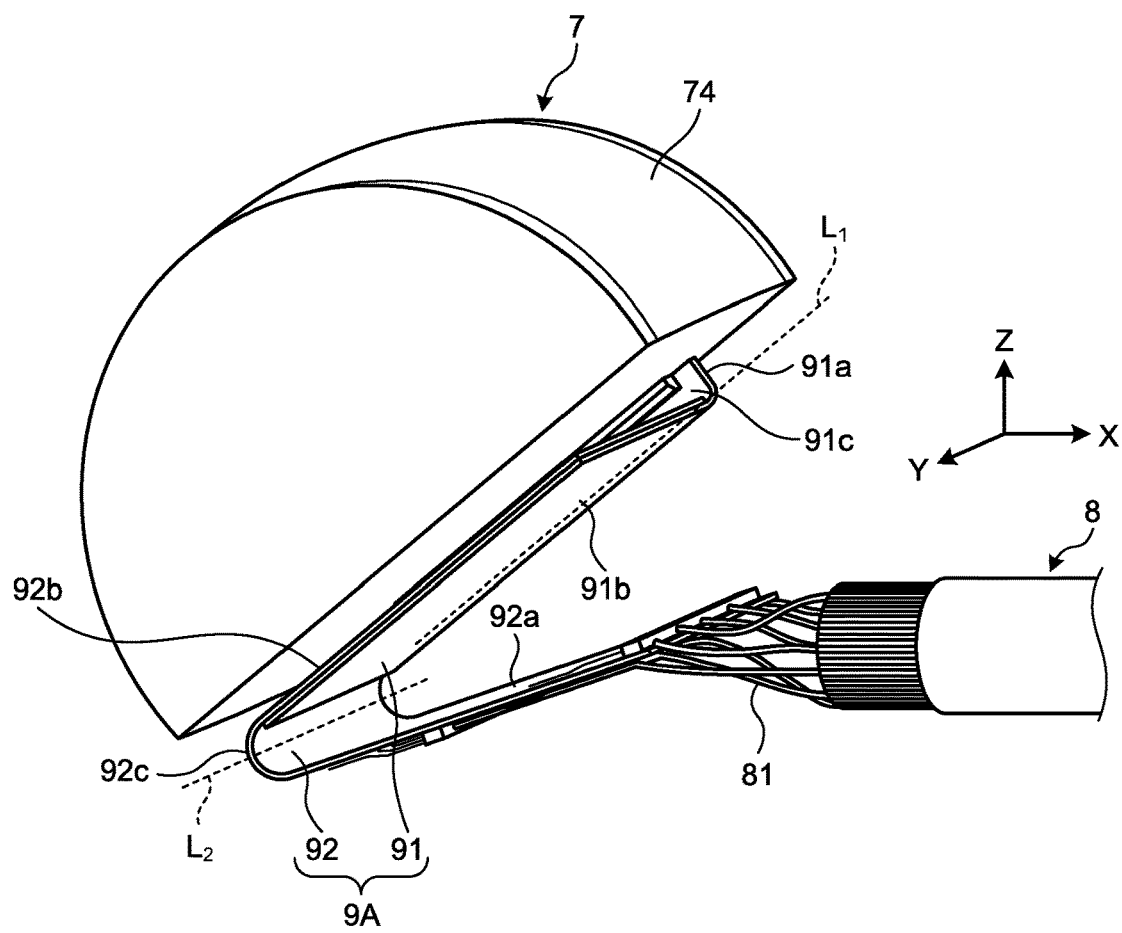
FIG. 7 is a perspective view schematically illustrating an internal configuration of an ultrasound function unit in an ultrasound endoscope according to a second embodiment of the disclosure.

FIG. 7 is a perspective view schematically illustrating an internal configuration of an ultrasound function unit in an ultrasound endoscope according to a second embodiment of the disclosure. In the first embodiment described above, it has been described that the relay substrate 9 is integrally formed, but in the second embodiment, the relay substrate is formed by linking two members. A relay substrate 9A illustrated in FIG. 7 includes a distal end side substrate 91 that is connected to the ultrasound transducer 7, and a proximal end side substrate 92 that is connected to the ultrasound cable 8 and is connected to the distal end side substrate 91.

Figure 8:
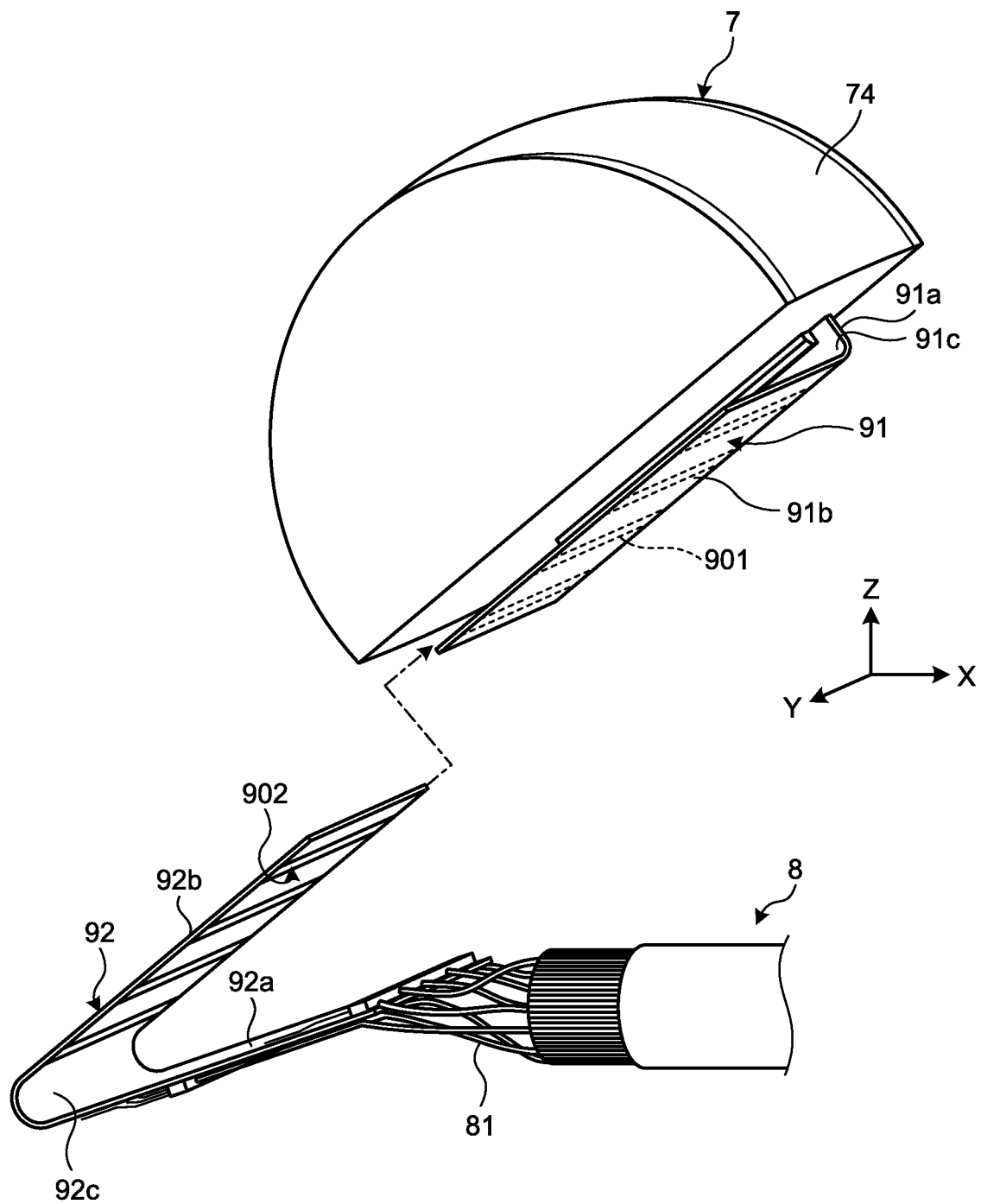
FIG. 8 is an exploded perspective view schematically illustrating the internal configuration of the ultrasound function unit in the ultrasound endoscope according to the second embodiment of the disclosure.
Figure 9:
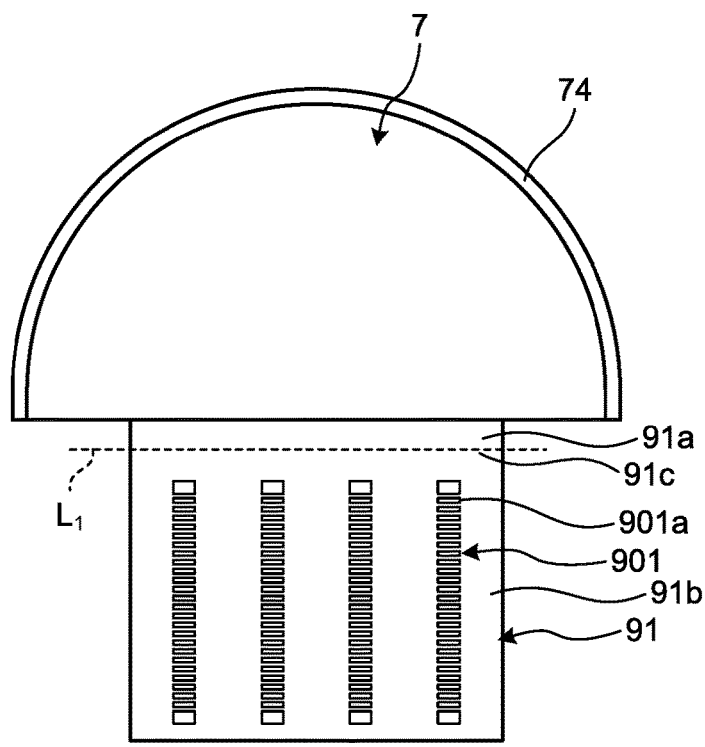
FIG. 9 is a view schematically illustrating a configuration of a part of the ultrasound function unit in the ultrasound endoscope according to the second embodiment of the disclosure.
Figure 10:
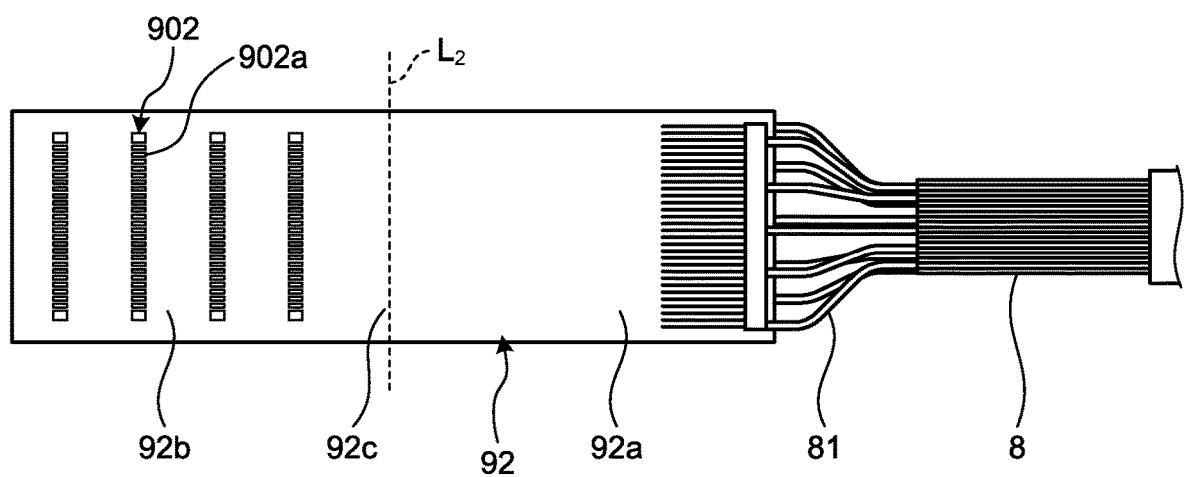
FIG. 10 is a view schematically illustrating the configuration of a part of the ultrasound function unit in the ultrasound endoscope according to the second embodiment of the disclosure.

FIG. 8 is an exploded perspective view schematically illustrating the internal configuration of the ultrasound function unit in the ultrasound endoscope according to the second embodiment of the disclosure. FIG. 9 is a view schematically illustrating the configuration of a part of the ultrasound function unit in the ultrasound endoscope according to the second embodiment of the disclosure, and is a view illustrating a configuration in which a curvature portion of the distal end side substrate 91 is drawn out. FIG. 10 is a view schematically illustrating the configuration of a part of the ultrasound function unit in the ultrasound endoscope according to the second embodiment of the disclosure, and is a view illustrating a configuration in which a curvature portion of the proximal end side substrate 92 is drawn out.

The distal end side substrate 91 includes a distal end side first portion 91a extending from the ultrasound transducer 7, and a distal end side second portion 91b including a main surface perpendicular to a main surface of the distal end side first portion 91a. The distal end side first portion 91a includes a main surface parallel to a plane that is parallel to a scanning surface of an ultrasound (the XZ plane of FIG. 7).

The distal end side second portion 91b includes a flexure portion 91c that is continuous to the distal end side first portion 91a (the first flexure portion).

The proximal end side substrate 92 includes a proximal end side first portion 92a that is connected to the ultrasound cable 8, and a proximal end side second portion 92b that is connected to the distal end side substrate 91 and includes a main surface facing the proximal end side first portion 92a through the distal end side second portion 91b.

The proximal end side second portion 92h includes a flexure portion 92c that is bent in a direction different from that of the flexure portion 91c and is continuous to the proximal end side first portion 92a (the second flexure portion).

The flexure portions 91c and 92c are bent in directions orthogonal to each other. Specifically, a straight line $L_1$ extending along a ridge line of a flexure end portion of the flexure portion 91c (the first straight line) and a straight line $L_2$ extending along a ridge line of a flexure end portion of the flexure portion 92c (the second straight line) are orthogonal to each other, in the plan view seen from a direction orthogonal to a main surface extending between the flexure portions 91c and 92c. In the second embodiment, the main surface extending between the flexure portions 91c and 92c is a main surface of the distal end side second portion 91b or the proximal end side second portion 92b. Note that, for the description, the straight lines $L_1$ and $L_2$ are illustrated in a development view illustrated in FIGS. 9 and 10, but in actuality, the straight lines $L_1$ and $l_2$ are along a ridge line that is generated when the flexure portion is bent.

In the distal end side second portion 91b of the distal end side substrate 91, an electrode group 901 including a plurality of electrodes 901a to be connected to the proximal end side substrate 92 is formed. On the other hand, in the proximal end side substrate 92, an electrode group 902 including a plurality of electrodes 902a to be respectively connected to the electrodes 901a formed in the distal end side second portion 91b of the distal end side substrate 91 is formed. The relay substrate 9A is bent in directions different from each other by connecting the corresponding electrodes 901a and 902a in the distal end side substrate 91 and the proximal end side substrate 92. In the connection between the electrodes 901a and 902a, a solder or a conductive adhesive agent is used.

The relay substrate 9A according to the second embodiment is bent in each of two different directions by the flexure portions 91c and 92c, in a state where the distal end side substrate 91 and the proximal end side substrate 92 are linked to each other. According to the second embodiment, even in a case where the curvature portion 212 is curved on the XY plane or is curved on the XZ plane at the time of being curved, two flexure portions of which the flexure directions are different from each other (the flexure portions 91c and 92c) are bent in accordance with the curvature, and thus, it is possible to relax the stress that is generated by the curvature. As described above, in the second embodiment, even in a case where the curvature portion that can be curved in two directions is curved in any direction, it is possible to relax a stress on the connection portion of the flexible substrate.

In addition, according to the second embodiment, the ultrasound cable 8 is connected to the proximal end side substrate 92, and then, the distal end side substrate 91 and the proximal end side substrate 92 are connected to each other, and thus, it is possible to wire up the ultrasound cable 8 with respect to the proximal end side substrate 92 in a lump. Accordingly, it is possible to more easily connect the ultrasound cable 8 to the proximal end side substrate 92.

Third Embodiment

Figure 11:
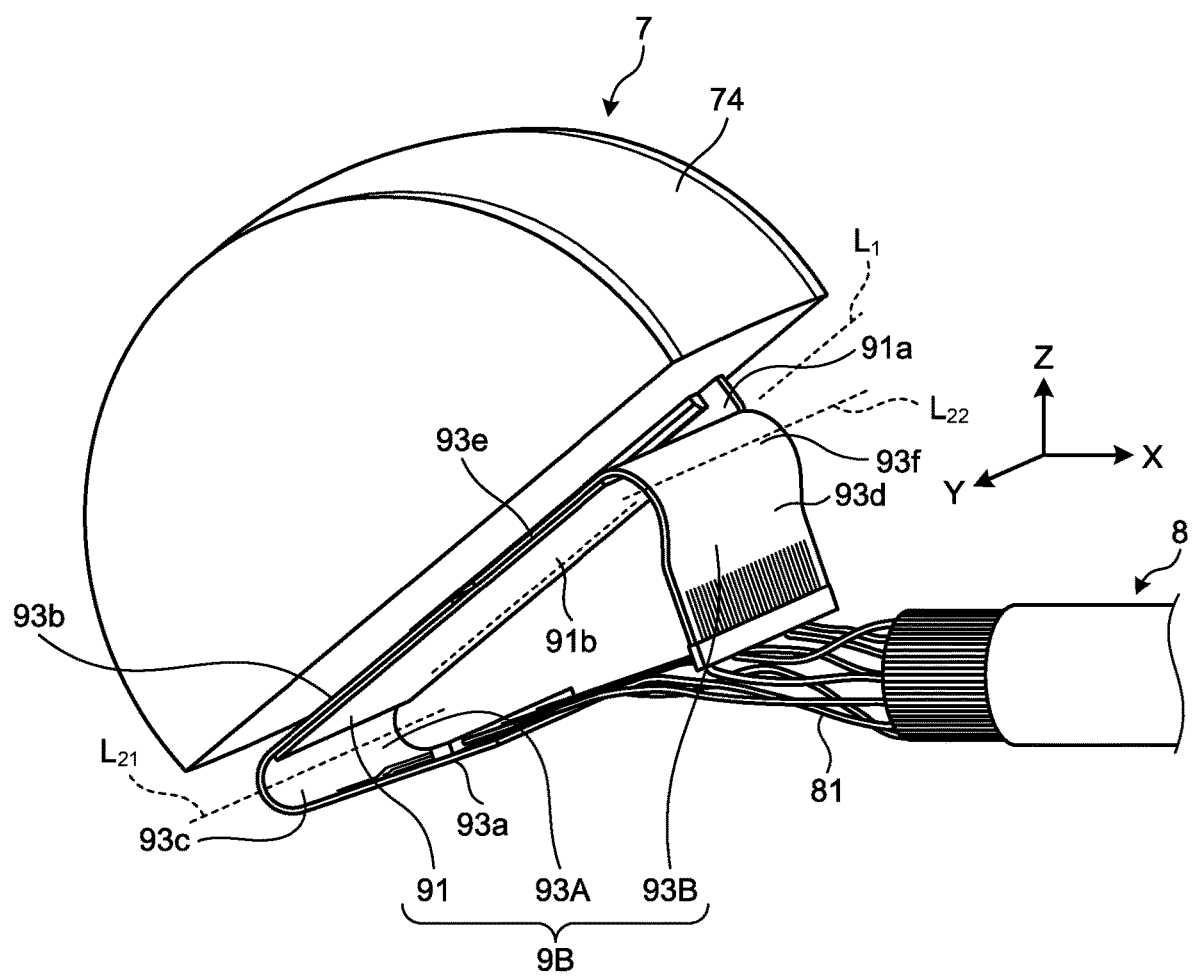
FIG. 11 is a perspective view schematically illustrating an internal configuration of an ultrasound function unit in an ultrasound endoscope according to a third embodiment of the disclosure.
Figure 12:
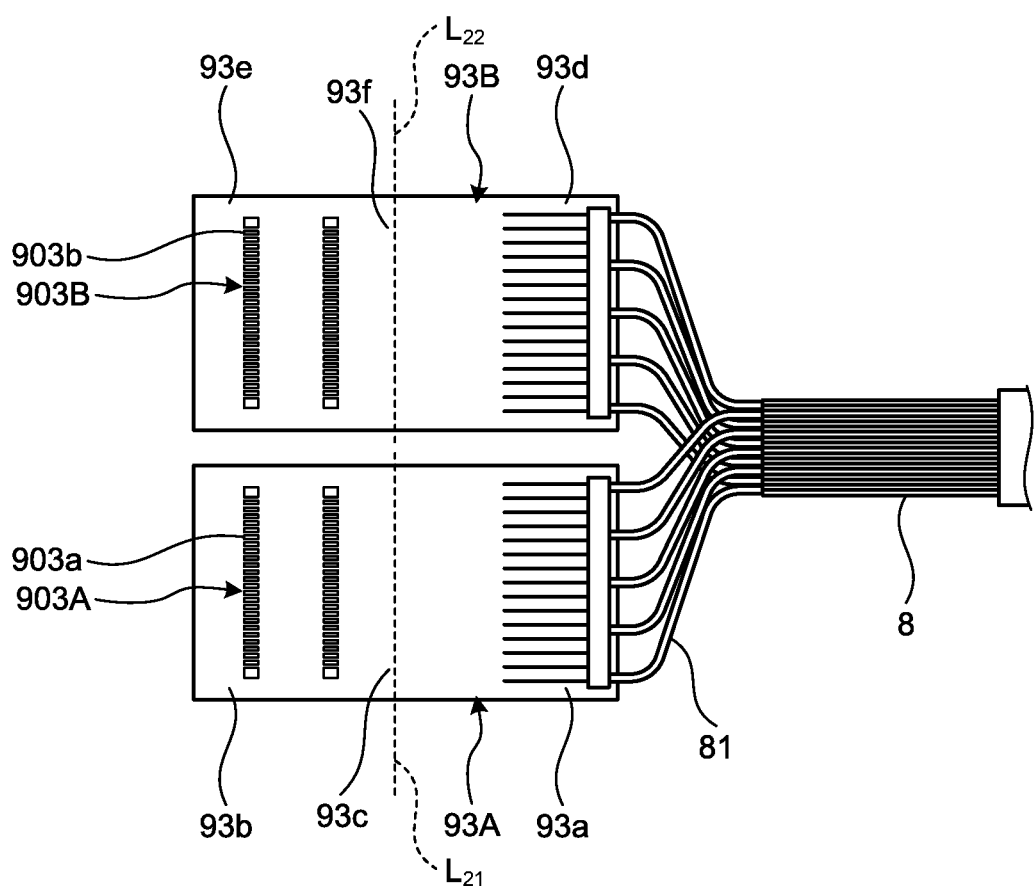
FIG. 12 is a view schematically illustrating a configuration of a part of the ultrasound function unit in the ultrasound endoscope according to the third embodiment of the disclosure.

FIG. 11 is a perspective view schematically illustrating an internal configuration of an ultrasound function unit in an ultrasound endoscope according to a third embodiment of the disclosure. FIG. 12 is a view schematically illustrating the configuration of a part of the ultrasound function unit in the ultrasound endoscope according to the third embodiment of the disclosure, and is a view illustrating a configuration in which curvature portions of a first substrate 93A and a second substrate 93B are drawn out. A relay substrate 9B illustrated in FIG. 11 includes the distal end side substrate 91 that is connected to the ultrasound transducer 7, and the first substrate 93A and the second substrate 93B that are each connected to the ultrasound cable 8 (hereinafter, may be collectively referred to as a proximal end side substrate 93), and links the distal end side substrate 91 and the proximal end side substrate 93.

The first substrate 93A is connected to a part of the plurality of coaxial wires 81 provided in the ultrasound cable 8.

The second substrate 93B is connected to a coaxial wire 81 different from the coaxial wire 81 that is connected to the first substrate 93A, in the plurality of coaxial wires 81 provided in the ultrasound cable 8

The first substrate 93A includes a proximal end side first portion 93a that is connected to the ultrasound cable 8, and a proximal end side second portion 93b that is connected to the distal end side substrate 91 and includes a main surface facing a main surface of the proximal end side first portion 93a.

The proximal end side second portion 93b includes a flexure portion 93c that is bent in a direction different from that of the flexure portion 91c and is continuous to the proximal end side first portion 93a (the second flexure portion). In the proximal end side second portion 93b, an electrode group 903A including a plurality of electrodes 903a to be respectively connected to a part of the plurality of electrodes 901a formed in the distal end side second portion 91b of the distal end side substrate 91 is formed.

The second substrate 93B includes a proximal end side first portion 93d that is connected to the ultrasound cable 8, and a proximal end side second portion 93e that is connected to the distal end side substrate 91 and includes a main surface facing a main surface of the proximal end side first portion 93d.

The proximal end side second portion 93e includes a flexure portion 93f that is bent in a direction different from that of the flexure portion 91c and is continuous to the proximal end side first portion 93d (the second flexure portion). In the proximal end side second portion 93e, an electrode group 903B including a plurality of electrodes 903b to be respectively connected to a part of the plurality of electrodes 901a formed in the distal end side second portion 91b of the distal end side substrate 91 is formed.

The relay substrate 9B disposes the first substrate 93A and the second substrate 93B on each of facing lateral surface sides, with respect to the distal end side substrate 91, and connects the corresponding electrode 901a and the electrode 903a or 903b, and thus, the flexure end portion is bent in directions opposite to each other.

At this time, the flexure portion 91c and the flexure portions 93c and 93f are bent in directions orthogonal to each other. Specifically, the straight line $L_1$ extending along the ridge line of the flexure end portion of the flexure portion 91c (the first straight line), and a straight line $L_{21}$ extending along a ridge line of a flexure end portion of the flexure portion 93c (the second straight line) and a straight line $L_{22}$ extending along a ridge line of a flexure end portion of the flexure portion 93f (the second straight line) are orthogonal to each other, in the plan view seen from a direction orthogonal to a main surface extending between the flexure portion 91c and the flexure portions 93c and 93f. In the third embodiment, the main surface extending between the flexure portion 91c and the flexure portions 93c and 93f is a main surface of the distal end side second portion 91b or the proximal end side second portion 93b or 93e.

The relay substrate 9B according to the third embodiment is bent in each of two different directions by the flexure portions 91c, 93c, and 93f, in a state where the proximal end side substrate 93 is linked to the distal end side substrate 91. According to the third embodiment, even in a case where the curvature portion 212 is curved on the XY plane or is curved on the XZ plane at the time of being curved, a plurality of flexure portions (the flexure portions 91c, 93c, and 93f) are bent in accordance with the curvature, and thus, it is possible to relax the stress that is generated by the curvature. As described above, in the third embodiment, even in a case where the curvature portion that can be curved in two directions is curved in any direction, it is possible to relax a stress on the connection portion of the flexible substrate.

Fourth Embodiment

Figure 13:
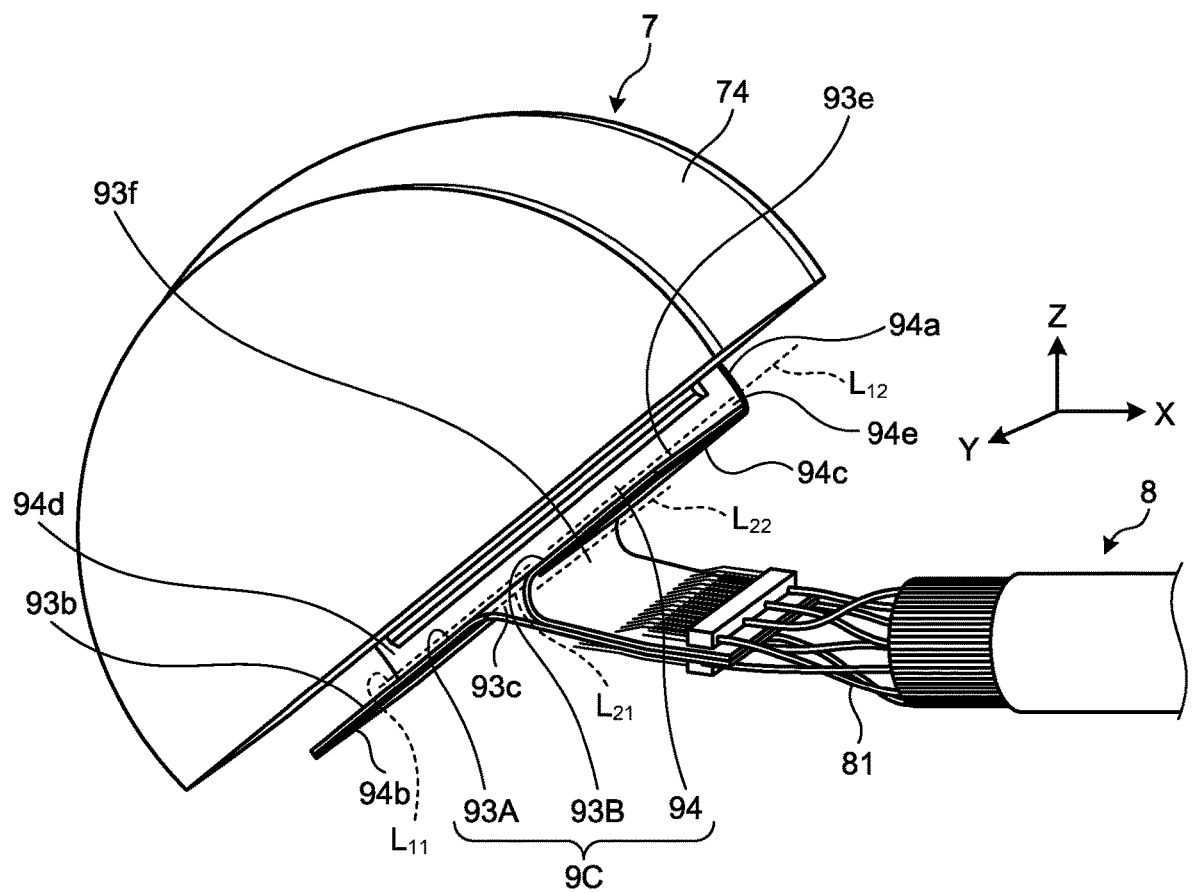
FIG. 13 is a perspective view schematically illustrating an internal configuration of as ultrasound function unit in an ultrasound endoscope according to a fourth embodiment of the disclosure.
Figure 14:
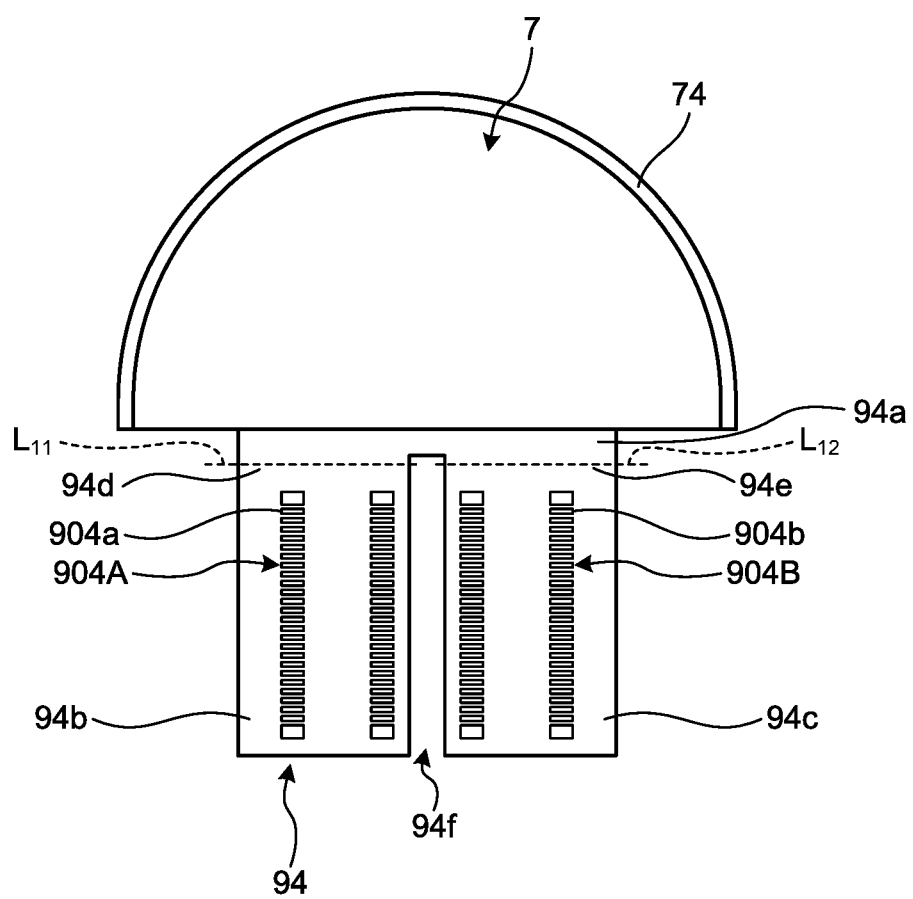
FIG. 14 is a view schematically illustrating a configuration of a part of the ultrasound function unit in the ultrasound endoscope according to the fourth embodiment of the disclosure.

FIG. 13 is a perspective view schematically illustrating an internal configuration of an ultrasound function unit in an ultrasound endoscope according to a fourth embodiment of the disclosure. FIG. 14 is a view schematically illustrating the configuration of a part of the ultrasound function unit in the ultrasound endoscope according to the fourth embodiment of the disclosure, and is a view illustrating a configuration in which a curvature portion of a distal end side substrate 94 is drawn out. A relay substrate 9C illustrated in FIG. 13 includes the distal end side substrate 94 that is connected to the ultrasound transducer 7, and the proximal end side substrates 93 that are each connected to the ultrasound cable 8. The proximal end side substrate 93 (the first substrate 93A and the second substrate 93B) is identical to that of the third embodiment described above, and thus, the description thereof will be omitted.

The distal end side substrate 94 includes a distal end side first portion 94a extending from the ultrasound transducer 7, and a distal end side second portion 94b and a distal end side third portion 94c including a main surface perpendicular to a main surface of the distal end side first portion 94a. The distal end side second portion 94b and the distal end side third portion 94c are separated from each other through a slit 94f.

The distal end side second portion 94b includes a flexure portion 94d that is continuous to the distal end side first portion 94a (the first flexure portion). The distal end side third portion 94c includes a flexure portion 94e that is continuous to the distal end side first portion 94a (the first flexure portion).

At this time, the flexure portions 94d and 94e and the flexure portions 93c and 93f are bent in directions orthogonal to each other. Specifically, a straight line In extending along a ridge line of a flexure end portion of the flexure portion 94d (the first straight line) and a straight line $L_{12}$ extending along a ridge line of a flexure end portion of a flexure portion 94e (the first straight line), and the straight line $L_{21}$ extending along the ridge line of the flexure end portion of the flexure portion 93c (the second straight line) and the straight line $L_{22}$ extending along the ridge line of the flexure end portion of the flexure portion 93f (the second straight line) are orthogonal to each other, in the plan view seen from a direction orthogonal to a main surface extending between the flexure portions 94d and 94e and the flexure portions 93c and 93f. In the fourth embodiment, the main surface extending between the flexure portions 94d and 94e and the flexure portions 93c and 93f is a main surface of the distal end side second portion 94b or the distal end side third portion 94c or the proximal end side second portion 93b or 93e. Note that, the straight line $L_{11}$ and the straight line $L_{21}$ are parallel to each other, and the straight line $L_{21}$ and the straight line $L_{22}$ are parallel to each other.

In the distal end side second portion 94b, an electrode group 904A including a plurality of electrodes 904a to be respectively connected to the electrodes 903a of the electrode group 903A formed on the first substrate 93A is formed on the main surface facing the ultrasound transducer 7.

In the distal end side third portion 94c, an electrode group 904B including a plurality of electrodes 904b to be respectively connected to the electrodes 903b of the electrode group 903B formed on the second substrate 93B is formed on the main surface facing the ultrasound transducer 7.

The relay substrate 9C is bent in directions different from each other by disposing each of the first substrate 93A and the second substrate 93B with respect to the distal end side substrate 94 through the slit 94f, and by connecting the corresponding electrode 904a and electrode 903a, the corresponding electrode 904b and electrode 903b.

The relay substrate 9C according to the fourth embodiment is bent in each of two different directions by the flexure portions 93c, 93f, 94d, and 94e, in a state where the distal end side substrate 94 and the proximal end side substrate 93 are linked to each other. According to the fourth embodiment, even in a case where the curvature portion 212 is curved on the KY plane or is curved on the XZ plane at the time of being curved, the plurality of flexure portions (the flexure portions 93c, 93f, 94d, and 94e) are bent in accordance with the curvature, and thus, it is possible to relax the stress that is generated by the curvature. As described above, in the fourth embodiment, even in a case where the curvature portion that can be curved in two directions is curved in any direction, it is possible to relax a stress on the connection portion of the flexible substrate.

Modification Example of Fourth Embodiment

Figure 15:
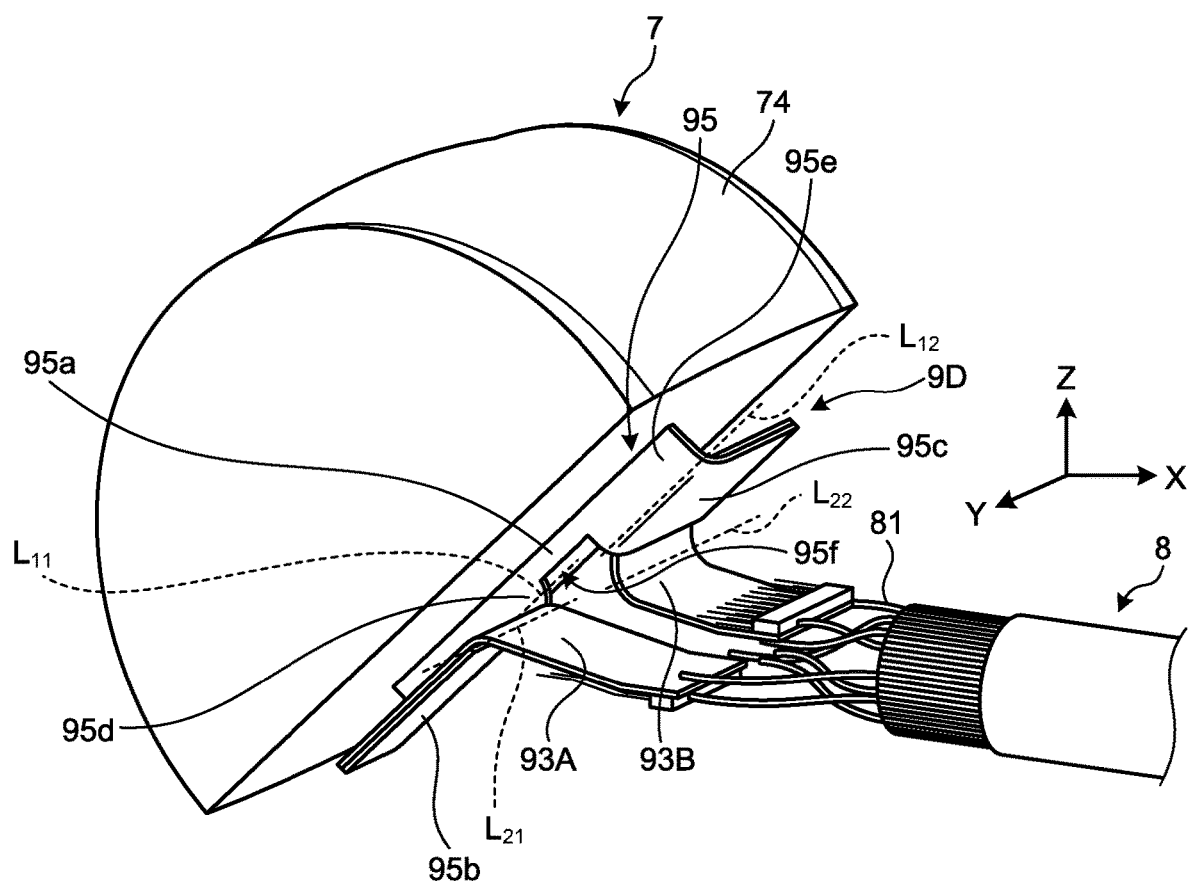
FIG. 15 is a perspective view schematically illustrating an internal configuration of an ultrasound function unit in an ultrasound endoscope according to a modification example of the fourth embodiment of the disclosure.
Figure 16:
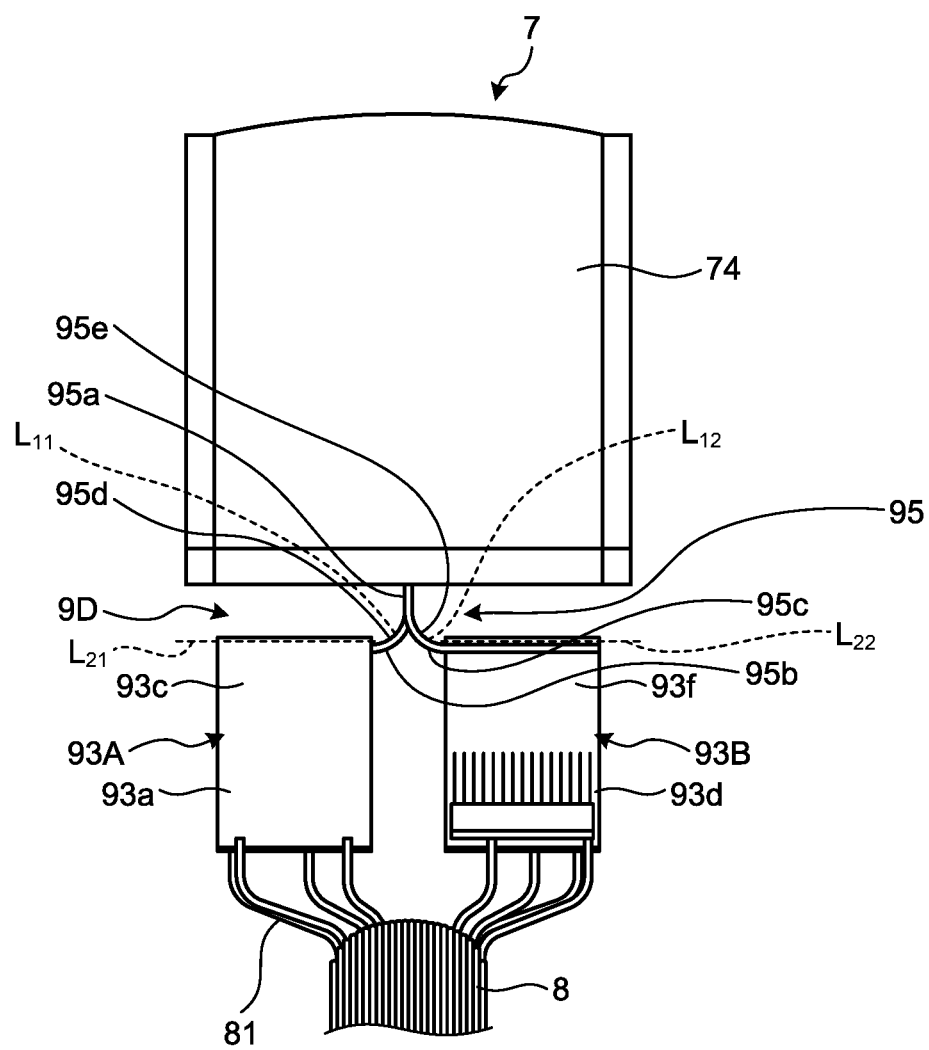
FIG. 16 is a perspective view schematically illustrating the internal configuration of the ultrasound function unit in the ultrasound endoscope according to the modification example of the fourth embodiment of the disclosure.

FIG. 15 and FIG. 16 are perspective views schematically illustrating an internal configuration of an ultrasound function unit in an ultrasound endoscope according to a modification example of the fourth embodiment of the disclosure. FIG. 16 is a view seen from a Y direction illustrated in FIG. 15. A relay substrate 9D illustrated in the same drawing includes a distal end side substrate 95 that is connected to the ultrasound transducer 7, and the proximal end side substrates 93 that are each connected to the ultrasound cable 8. The proximal end side substrate 93 (the first substrate 93A and the second substrate 93B) is identical to that of the third embodiment described above, and thus, the description thereof will be omitted.

The distal end side substrate 95 includes a distal end side first portion 95a extending from the ultrasound transducer 7, and a distal end side second portion 95b and a distal end side third portion 95c including a main surface perpendicular to a main surface of the distal end side first portion 95a. The distal end side second portion 95b and the distal end side third portion 95c are separated from each other through a slit 95f.

The distal end side second portion 95b includes a flexure portion 95d that is continuous to the distal end side first portion 95a (the first flexure portion). The distal end side third portion 95c includes a flexure portion 95e that is continuous to the distal end side first portion 95a (the first flexure portion). In the flexure portions 95d and 95e, flexure end portions are bent in directions opposite to each other.

At this time, the flexure portions 95d and 95e and the flexure portions 93c and 93f are bent in directions orthogonal to each other. Specifically, a straight line $L_{11}$ extending along a ridge line of a flexure end portion of the flexure portion 95d (the first straight line) and a straight line $L_{12}$ extending along a ridge line of a flexure end portion of the flexure portion 95e (the first straight line), and the straight line $L_{21}$ extending along the ridge line of the flexure end portion of the flexure portion 93c and the straight line $L_{22}$ extending along the ridge line of the flexure end portion of the flexure portion 93f are orthogonal to each other, in the plan view seen from a direction orthogonal to a main surface extending between the flexure portions 95d and 95e and the flexure portions 93c and 93f. In the modification example, the main surface extending between the flexure portions 95d and 95e and the flexure portions 93c and 93f is a main surface of the distal end side second portion 95b or the distal end side third portion 95c or the proximal end side second portion 93b or 93e. Note that, the straight line $L_{11}$ and the straight line $L_{12}$ are parallel to each other.

In the distal end side second portion 95b, an electrode group (not illustrated) including a plurality of electrodes to be respectively connected to the electrodes 903a of the electrode group 903A formed on the first substrate 93A is formed on the main surface facing the ultrasound transducer 7.

In the distal end side third portion 95c, an electrode group (not illustrated) including a plurality of electrodes to be respectively connected to the electrodes 903b of the electrode group 903B formed on the second substrate 93B is formed on the main surface facing the ultrasound transducer 7.

The distal end side substrate 95, for example, has a shape in which the electrode group 904B of the distal end side third portion 94c of the distal end side substrate 94 described above is formed on a main surface on an opposite side, and is bent in an opposite direction.

The relay substrate 9D is bent in directions different from each other by reversing curvature directions of the first substrate 93A and the second substrate 93B, with respect to the distal end side substrate 95, and by connecting the corresponding electrodes.

The relay substrate 9D according to the modification example is bent in each of two different directions by the flexure portions 93c, 93f, 95d, and 95e, in a state where the distal end side substrate 95 and the proximal end side substrate 93 are linked to each other. According to the modification example, even in a case where the curvature portion 212 is curved on the XY plane or is curved on the XZ plane at the time of being curved, the plurality of flexure portions (the flexure portions 93c, 93f, 95d, and 95e) are bent in accordance with the curvature, and thus, it is possible to relax the stress that is generated by the curvature. As described above, in the modification example, even in a case where the curvature portion that can be curved in two directions is curved in any direction, it is possible to relax a stress on the connection portion of the flexible substrate.

Fifth Embodiment

Figure 17:
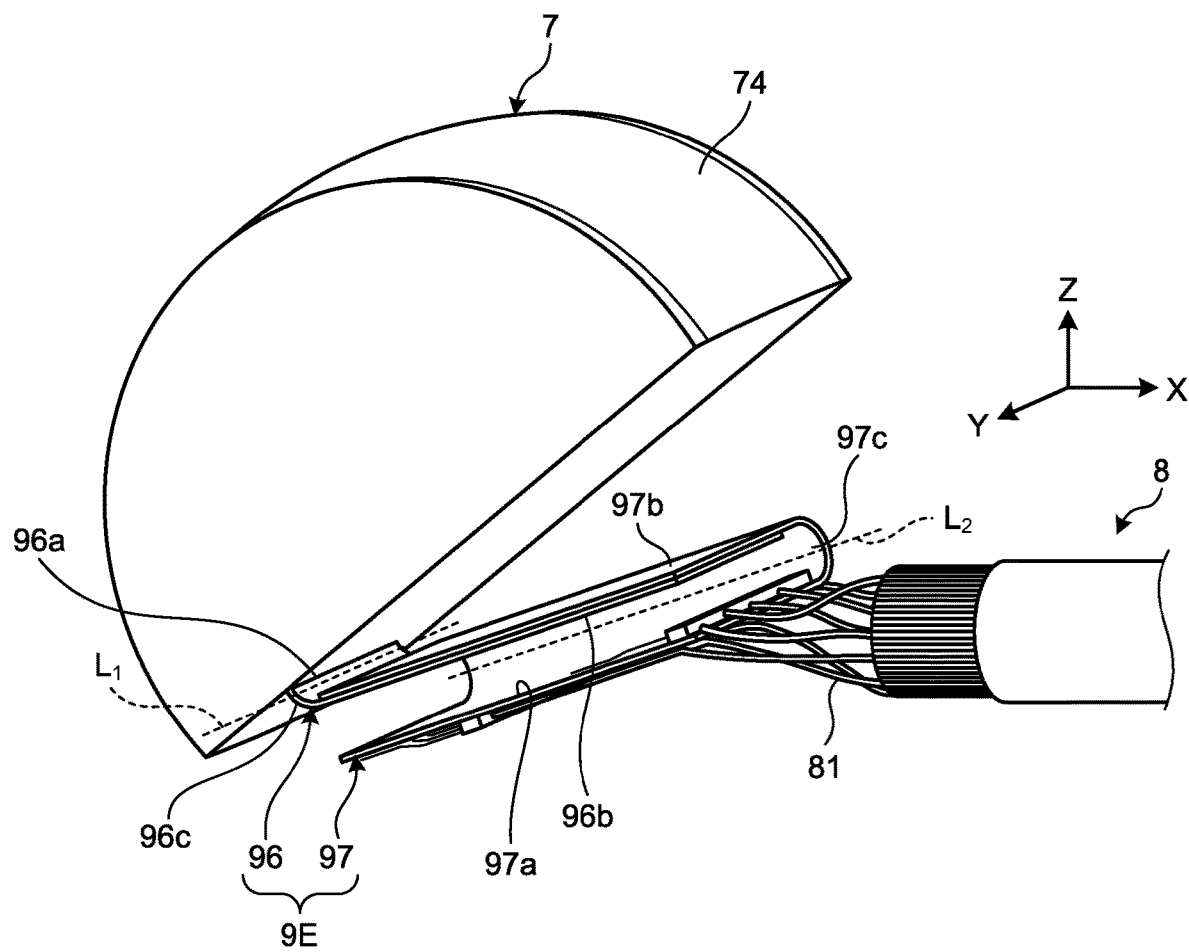
FIG. 17 is a perspective view schematically illustrating an internal configuration of an ultrasound function unit in an ultrasound endoscope according to a fifth embodiment of the disclosure.
Figure 18:
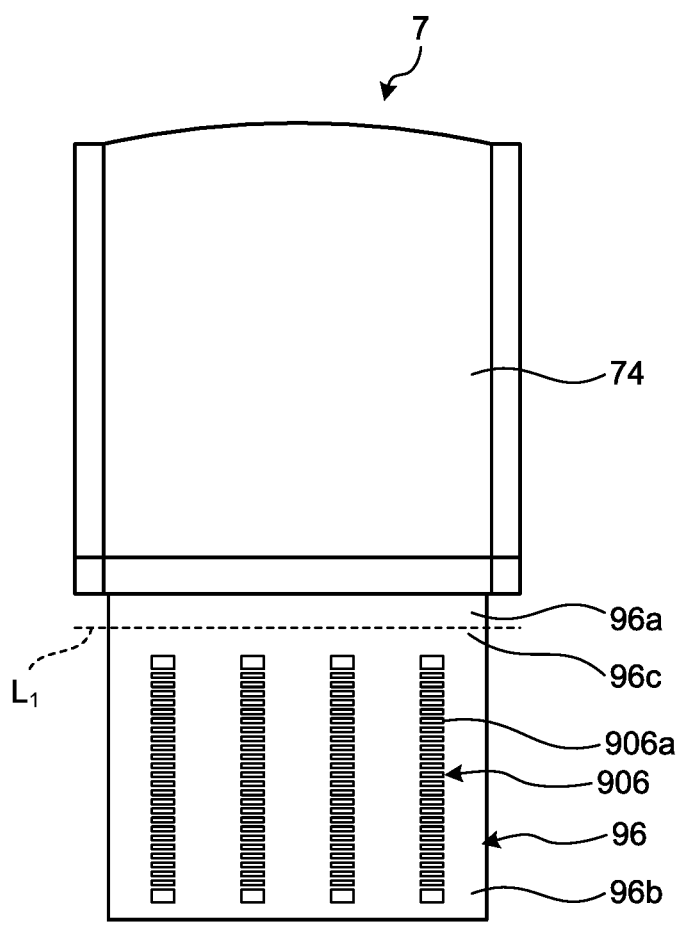
FIG. 18 is a view schematically illustrating a configuration of a part of the ultrasound function unit in the ultrasound endoscope according to the fifth embodiment of the disclosure.
Figure 19:
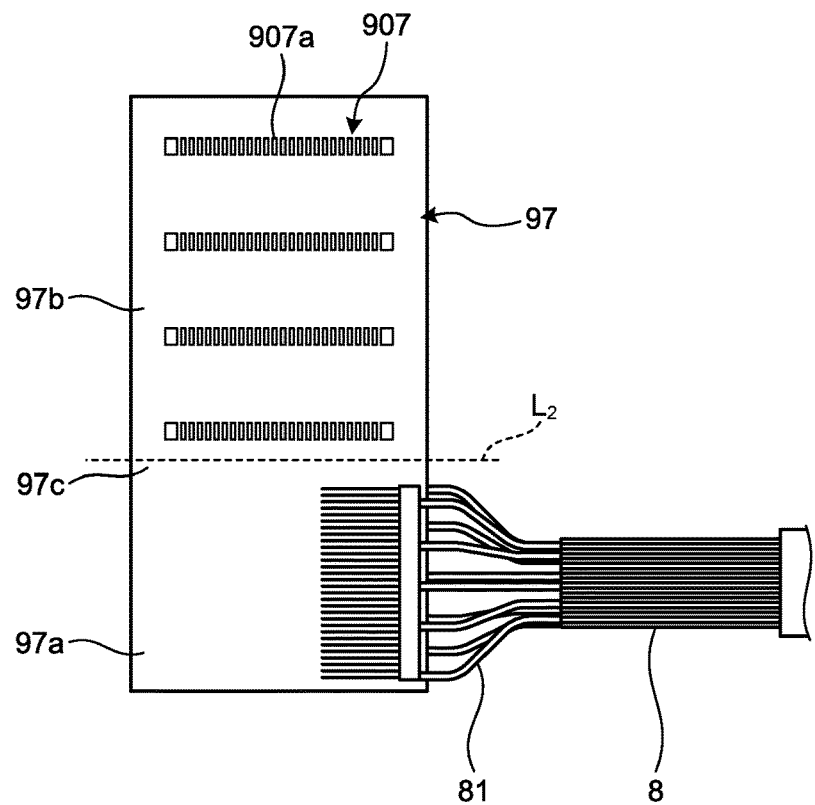
FIG. 19 is a view schematically illustrating the configuration of a part of the ultrasound function unit in the ultrasound endoscope according to the fifth embodiment of the disclosure.

FIG. 17 is a perspective view schematically illustrating an internal configuration of an ultrasound function unit in an ultrasound endoscope according to a fifth embodiment of the disclosure. FIG. 18 is a view schematically illustrating the configuration of a part of the ultrasound function unit in the ultrasound endoscope according to the fifth embodiment of the disclosure, and is a view illustrating a configuration in which a curvature portion of a distal end side substrate 96 is drawn out. FIG. 19 is a view schematically illustrating the configuration of a part of the ultrasound function unit in the ultrasound endoscope according to the fifth embodiment of the disclosure, and is a view illustrating a configuration in which a curvature portion of a proximal end side substrate 97 is drawn out. A relay substrate 9E illustrated in FIG. 17 includes a distal end side substrate 96 that is connected to the ultrasound transducer 7, and a proximal end side substrate 97 that is connected to the ultrasound cable 8.

The distal end side substrate 96 includes a distal end side first portion 96a extending from the ultrasound transducer 7, and a distal end side second portion 96b that extends in a direction different from that of the distal end side first portion 96a and is linked to the proximal end side substrate 97. The distal end side first portion 96a includes a main surface orthogonal to a plane parallel to the scanning surface of the ultrasound (the XZ plane of FIG. 17). For example, the distal end side substrate 96 is disposed to be rotated by 90° with respect to the distal end side substrate 91 of the second embodiment described above. The distal end side second portion 96b includes a flexure portion 96c that connects the distal end side first portion 96a and the distal end side second portion 96b (the first flexure portion).

The proximal end side substrate 97 includes a proximal end side first portion 97a that is connected to the ultrasound cable 8, and a proximal end side second portion 97b that is connected to the distal end side substrate 96 and includes a main surface facing the proximal end side first portion 97a through the distal end side second portion 96b. The proximal end side second portion 97b includes a flexure portion 97c that is bent in a direction different from that of the flexure portion 96c and is continuous to the proximal end side first portion 97a (the second flexure portion).

At this time, the flexure portion 96c and the flexure portion 97c are bent in directions orthogonal to each other. Specifically, a straight line $L_1$ extending along a ridge line of a flexure end portion of the flexure portion 96c (the first straight line) and a straight line $L_2$ extending along a ridge line of a flexure end portion of the flexure portion 97c (the second straight line) are orthogonal to each other, in the plan view seen from a direction orthogonal to a main surface extending between the flexure portions 96c and 97c. In the fifth embodiment, the main surface extending between the flexure portions 96c and 97c is a main surface of the distal end side second portion 96b or the proximal end side second portion 97b.

In the distal end side second portion 96b of the distal end side substrate 96, an electrode group 906 including a plurality of electrodes 906a to be connected to the proximal end side substrate 97 is formed (refer to FIG. 18). On the other hand, in the proximal end side substrate 97, an electrode group 907 including a plurality of electrodes 907a to be respectively connected to the electrodes 906a formed in the distal end side second portion 96b of the distal end side substrate 96 is formed (refer to FIG. 19). The relay substrate 9E is bent in directions different from each other by connecting the corresponding electrodes 906a and 907a in the distal end side substrate 96 and the proximal end side substrate 97. The relay substrate 9E has a shape in which curved states of the distal end side substrate 91 and the proximal end side substrate 92 of the relay substrate 9A described above are reversed.

The relay substrate 9E according to the fifth embodiment is bent in each of two different directions by the flexure portions 96c and 97c, in a state where the distal end side substrate 96 and the proximal end side substrate 97 are linked to each other. According to the fifth embodiment, even in a case where the curvature portion 212 is curved on the XY plane or is curved on the XZ plane at the time of being curved, two flexure portions of which the flexure directions are different from each other (the flexure portions 96c and 97c) are bent in accordance with the curvature, and thus, it is possible to relax the stress that is generated by the curvature. As described above, in the fifth embodiment, even in a case where the curvature portion that can be curved in two directions is curved in any direction, it is possible to relax a stress on the connection portion of the flexible substrate.

Sixth Embodiment

Figure 20:
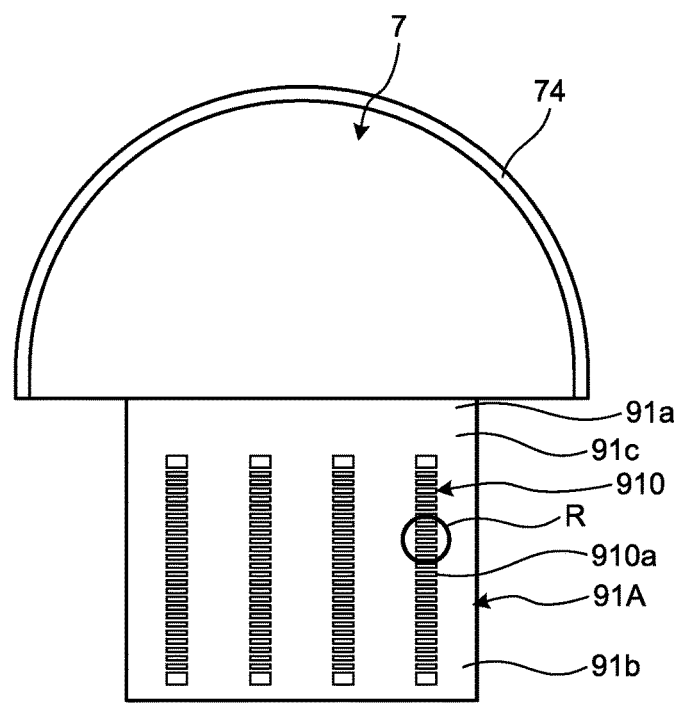
FIG. 20 is a view schematically illustrating a configuration of a part of an ultrasound function unit in an ultrasound endoscope according to a sixth embodiment of the disclosure.
Figure 21:
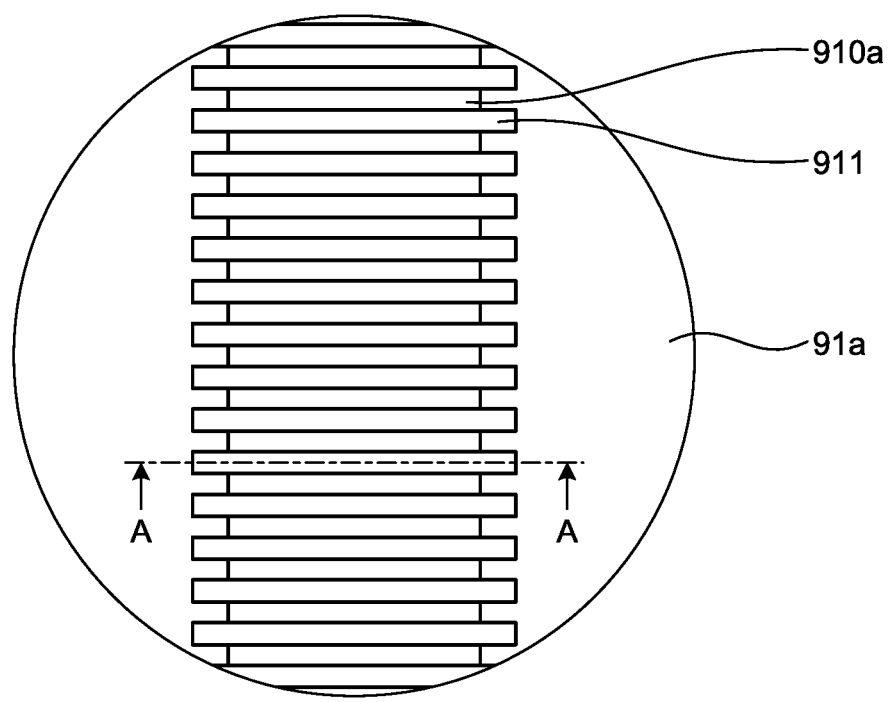
FIG. 21 is an enlarged view of a region R of FIG. 20.
Figure 22:
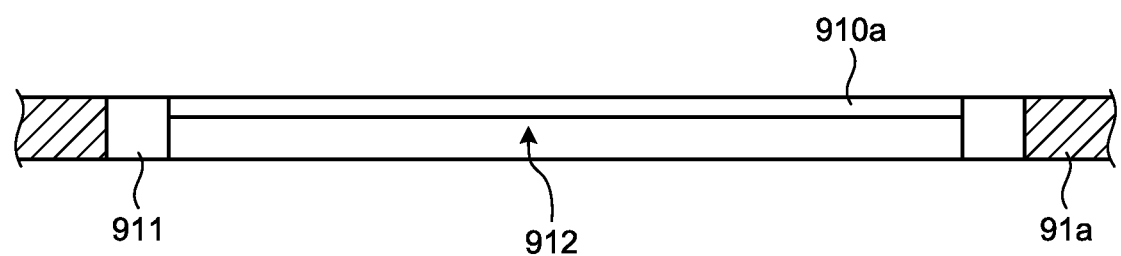
FIG. 22 is a sectional view of line A-A illustrated in FIG. 21.

FIG. 20 is a views schematically illustrating the configuration of a part of an ultrasound function unit in an ultrasound endoscope according to a sixth embodiment of the disclosure, and is a view illustrating a configuration in which a curvature portion of a distal end side substrate 91A according to the sixth embodiment is drawn out. FIG. 21 is an enlarged view of a region R of FIG. 20. FIG. 22 is a sectional view of line A-A illustrated in FIG. 21. The overall shape of the distal end side substrate 91A in the ultrasound transducer module according to the sixth embodiment is identical to that of the distal end side substrate 91 illustrated in FIG. 6. In the sixth embodiment, the configuration of an electrode in the distal end side substrate 91A is different from that of the distal end side substrate 91, and thus, here, only the configuration of the electrode will be described.

The distal end side substrate 91A includes the distal end side first portion 91a, the distal end side second portion 91b, and the flexure portion 91c. In the distal end side second portion 91b, an electrode group 910 including a plurality of electrodes 910a to be connected to the proximal end side substrate 92 is formed. In the distal end side second portion 91b, slits 911 are arranged in the longitudinal direction and are formed between the adjacent electrodes 910a in an arrangement direction, and a space 912 formed on a rear surface of the electrode 910a. Each of the electrodes 910a has a flying lead structure by a space that is formed by the slit 911 and the space 912, a movable range due to the flexure of the proximal end side substrate 92 increases compared to a case where the slit 911 or the space 912 is not provided. In the sixth embodiment, the electrode 910a has the flying lead structure, and thus, it is possible to absorb a stress from the proximal end side substrate 92 by the electrode 910a.

Note that, in the sixth embodiment described above, it has been described that the flying lead structure is formed in the electrode of the distal end side second portion 91b of the distal end side substrate 91A, but the flying lead structure may be formed in the electrode of the proximal end side second portion 92b of the proximal end side substrate 92.

The modes for carrying out the disclosure have been described, but the disclosure is not limited to the embodiments and the modification example described above. The disclosure is not limited to the embodiments and the modification examples described above, but is capable of including various embodiments within a range not departing from the technical ideas described in the claims. In addition, the configurations of the embodiments and the modification examples may be suitably combined.

In addition, in the first embodiment to the sixth embodiment described above, a cutout is Provided in the flexure portion of each of the substrates, or the thickness of the flexure portion is set to be less than the thicknesses of the other portions, and thus, the rigidity of the flexure portion may be decreased compared to the other portions to be easily modified. In addition, the portions other than the flexure portion (the distal end side portion and/or the proximal end side portion) may be formed by using a rigid material, and thus, the flexure portion may be more actively modified with respect to a stress.

Figure 23:
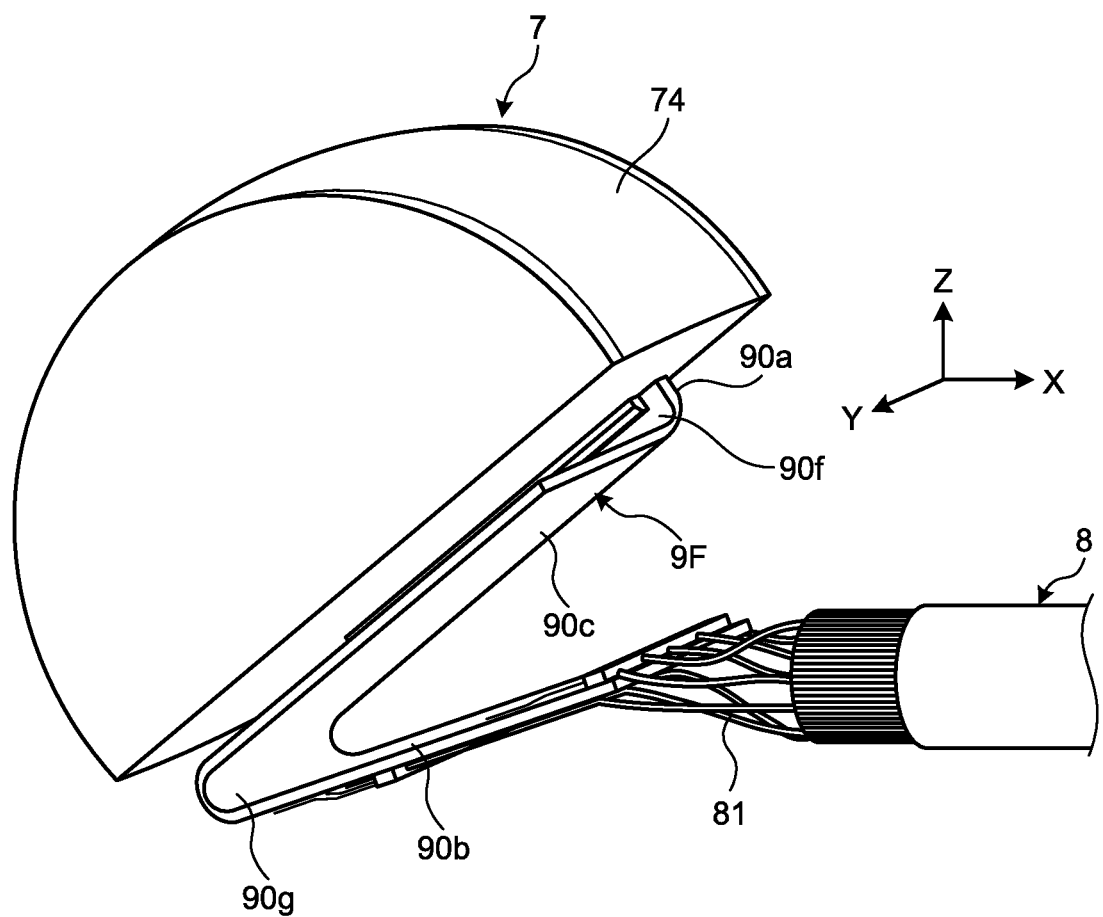
FIG. 23 is a perspective view schematically illustrating an internal configuration of an ultrasound function unit in an ultrasound endoscope according to another embodiment of the disclosure.

FIG. 23 is a perspective view schematically illustrating an internal configuration of an ultrasound function unit in an ultrasound endoscope according to other embodiments of the disclosure. For example, as with a relay substrate 9F illustrated in FIG. 23, the third portion 90c may include flexure portions 90f and 90g having a thickness that is less than the thicknesses of the first portion 90a and the second portion 90b.

In addition, in the first embodiment to the sixth embodiment described above, it has been described that the piezoelectric element allows an ultrasound to exit and converts an ultrasound incident from the outside into an echo signal, as an example, but the disclosure is not limited thereto, and an element manufactured by using a micro electro mechanical systems (MEMS), for example, capacitive micromachined ultrasonic transducers (C-MUT) or piezoelectric micromachined ultrasonic transducers (P-MUT) may be used.

In addition, a thin ultrasound probe performing scanning by mechanically rotating a transducer but not an optical system may be applied as the ultrasound endoscope. In general, the ultrasound probe is inserted into the bile passage, the bile duct, the ductus pancreaticus, the trachea, the bronchial tube, the urethra, and the urinary duct, and is used at the time of observing the surrounding internal organ (the pancreas, the bellows, the prostate, the urinary bladder, the lymphaden, and the like).

In addition, the ultrasound transducer may be a linear transducer, a radial transducer, or a convex transducer. In a case where the ultrasound transducer is the linear transducer, a scanning region thereof is in the shape of a quadrangle (a rectangle and a square), and in a case where the ultrasound transducer is the radial transducer or the convex transducer, the scanning region is in the shape of a sector or a circular ring. In addition, in the ultrasound endoscope, the ultrasound transducer may perform mechanical scanning, or a plurality of elements may be provided into the shape of an array, as the ultrasound transducer, and the elements involved in the transmission and reception may be electronically switched or the transmission and reception of each of the elements may be delayed, and thus, electronic scanning may be performed.

In addition, an external ultrasound probe emitting an ultrasound from the body surface of the subject may be applied as the ultrasound endoscope. In general, the external ultrasound probe is used at the time of observing the abdominal organ (the liver, the bladder, the urinary bladder), the breast Mass (in particular, the lacteal gland), and the glandula thyreoidea.

Note that, in the first embodiment to the sixth embodiment described above, the ultrasound endoscope including the ultrasound transducer on the distal end has been described as an example, but an endoscope not including the ultrasound transducer, for example, an endoscope including only the endoscope module 215 on the distal end can also be applied. In the case of the endoscope, the configurations of the first embodiment to the sixth embodiment described above can be applied, in a configuration including a relay substrate connected to an image sensor and a cable extending to a connector from the relay substrate.

In addition, in the first embodiment to the sixth embodiment described above, the ultrasound endoscope in which the insertion portion 21 includes the flexible tube portion 213 has been described as an example, but an endoscope provided with an insertion portion including a rigid tube portion instead of the flexible tube portion 213, that is, a rigid endoscope can also be applied.

As described above, the endoscope according to the disclosure is useful for relaxing the stress on the connection portion of the flexible substrate even in a case where the curvature portion that can be curved in two directions is curved in any direction.

According to the disclosure, an effect is obtained in which it is possible to relax a stress to be applied to a connection portion of a flexible substrate even in a case where a curvature portion that can be curved in two directions is curved in any direction.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope, comprising:
   a distal end portion provided on a distal end of an insertion portion, the insertion portion being configured to be inserted into a subject;
   a curvature portion connected to a proximal end side of the distal end portion, the curvature portion being configured to be curved in first and second curvature directions orthogonal to each other;
   a plurality of coaxial wires inserted into the curvature portion in a longitudinal axis direction of the insertion portion;
   a convex ultrasound transducer including a first surface is configured to transmit and receive an ultrasound and a second surface provided on a side opposite to the first surface, the convex ultrasound transducer being provided in the distal end portion such that the second surface is inclined relative to the longitudinal axis;
   a first relay substrate electrically connected to the ultrasound transducer, the first relay substrate comprising a first-first relay substrate and a second-first relay substrate surface, the first-first relay substrate connected to the first surface, the second-first relay substrate having the plurality of first electrodes; and
   a second relay substrate electrically connected to the plurality of coaxial wires, the second relay substrate comprising a first-second relay substrate and a second-second relay substrate, the first-second relay substrate connected to the plurality of coaxial wires, the second-second relay substrate having the plurality of second electrodes;
   wherein the second-first relay substrate overlaps the second-second relay substrate in a direction orthogonal to the second surface,
   the plurality of first electrodes are electrically connected to the plurality of second electrodes, and
   the first relay substrate and the second relay substrate are at least partially disposed within a space defined by a projection of the second surface in the direction orthogonal to the second surface.

2. The ultrasound endoscope according to claim 1, wherein the first relay substrate comprising a first flexure, the first flexure being provided between the first-first relay substrate and the second-first relay substrate, the first flexure being bent such that the second-first relay substrate is parallel to the second surface.

3. The ultrasound endoscope according to claim 1, wherein the second relay substrate comprising a second flexure, the second flexure being provided between the first-second relay substrate and the second-second relay substrate, the second flexure being bent from a distal end of the distal end portion to the proximal end of the distal end portion.

4. The ultrasound endoscope according to claim 1, wherein the plurality of first electrodes directly contact with the plurality of second electrodes.

5. The ultrasound endoscope according to claim 1, wherein the second-first relay substrate overlaps only the second-second relay substrate.

6. The ultrasound endoscope according to claim 1, wherein the first relay substrate and the second relay substrate are formed separately.

* * * * *